US011819416B1

(12) United States Patent
Roh et al.

(10) Patent No.: US 11,819,416 B1
(45) Date of Patent: Nov. 21, 2023

(54) DESIGNING AND MANUFACTURING PROSTHETIC IMPLANTS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael J. Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/884,005

(22) Filed: Aug. 9, 2022

(51) Int. Cl.
*A61F 2/46* (2006.01)
*A61F 2/30* (2006.01)

(52) U.S. Cl.
CPC ........ *A61F 2/30942* (2013.01); *A61F 2/4603* (2013.01); *A61F 2002/3096* (2013.01); *A61F 2002/30736* (2013.01); *A61F 2002/30943* (2013.01); *A61F 2002/30952* (2013.01); *A61F 2002/30985* (2013.01); *A61F 2002/4633* (2013.01)

(58) Field of Classification Search
CPC ........ A61F 2/30942; A61F 2002/30736; A61F 2002/30985; A61F 2002/4633
See application file for complete search history.

(56) References Cited

U.S. PATENT DOCUMENTS

| 8,532,807 | B2 | 9/2013 | Metzger | |
|---|---|---|---|---|
| 2014/0228860 | A1* | 8/2014 | Steines | A61B 34/30 606/130 |
| 2014/0371897 | A1* | 12/2014 | Lin | G05B 19/4099 700/118 |
| 2016/0231732 | A1 | 8/2016 | Neetz | |
| 2017/0203509 | A1 | 7/2017 | Stieghorst et al. | |
| 2018/0326484 | A1* | 11/2018 | Bonilla Gonzalez | B22F 3/1021 |
| 2022/0354653 | A1 | 11/2022 | Minocha et al. | |

FOREIGN PATENT DOCUMENTS

| EP | 0538276 | 12/1996 |
|---|---|---|
| WO | WO 2009/134672 | 11/2009 |

* cited by examiner

*Primary Examiner* — Brian A Dukert
(74) *Attorney, Agent, or Firm* — Fish & Richardson P.C.

(57) ABSTRACT

Systems, methods, and techniques for customizing connectors for connecting standardized implant components together or to a part of a patient. The connectors are customized based on medical imagery of the patient and/or other patient data and may use additive or subtractive manufacturing techniques. The connectors can be manufactured at the point of use and used with standardized components.

29 Claims, 8 Drawing Sheets

Patient Database

| Patient ID | Age | Gender | Height (in.) | Allergies | Conditions | Image Files |
|---|---|---|---|---|---|---|
| M_0026 | 46 | Male | 70 | None | None | MRI_pelvis_3-20-2022 |
| F_0165 | 36 | Female | 65 | None | None | XRAY_r-knee_2-4-2022 |
| F_0654 | 48 | Female | 68 | Latex | Breast Cancer | CT_chest_1-5-2022 |
| M_0264 | 65 | Male | 72 | None | Coronary Heart Disease | CT_chest_2-16-2022 |
| F_0544 | 72 | Female | 63 | None | Osteoporosis | XRAY_pelvis_2-25-2022 |

FIG. 3

Implant Database

| Implant ID | Implant Component ID | Materials | Mechanisms | Width (cm) | Height (cm) | Length (cm) |
|---|---|---|---|---|---|---|
| A364 | 135 | Titanium Alloy | Butterfly hinges | 1.5 | 1 | 6 |
| A364 | 136 | Polypropylene | None | 2 | 1 | 3 |
| A364 | 137 | Cobalt-chromium Alloy | None | 1 | 2.5 | 5 |
| A364 | 138 | Medical-grade Silicone | None | 2 | 2 | 10 |
| A364 | 139 | Polyvinylchloride | None | 1 | 2 | 4 |
| A364 | 140 | Polyethylene | None | 1 | 2 | 4.5 |
| A364 | 141 | Polypropylene | None | 3 | 1.5 | 7 |
| A364 | 142 | Stainless Steel | Expanding mesh | 1 | 1 | 5 |
| A364 | 143 | Titanium | Telescoping tubing | 0.5 | 0.5 | 5 |
| A364 | 144 | Ziconia | None | 1.5 | 1.5 | 3 |

FIG. 4

Substrate Database

| Substrate ID | Material | Material Type | Extrusion Method | Curing Method |
|---|---|---|---|---|
| 135 | UV Curable Resin | Resin | Pumped Gel | Ultraviolet Light |
| 136 | Alumina | Compound | Extruded Paste | Laser Sintering |
| 137 | Cobalt-chromium Alloy | Metal Alloy | Extruded Paste | Laser Sintering |
| 138 | Medical-grade Silicone | Resin | Pumped Gel | Two Part Cure |
| 139 | Polyvinylchloride | Thermoplastic | Extruded Melted Plastic | Cooling |
| 140 | Polyethylene | Thermoplastic | Extruded Melted Plastic | Cooling |
| 141 | Polypropylene | Thermoplastic | Extruded Melted Plastic | Cooling |
| 142 | Stainless Steel | Metal | Powder in Binder | Laser Sintering |
| 143 | Titanium | Metal | Powder in Binder | Laser Sintering |
| 144 | Ziconia | Ceramic | Powder in Binder | Laser Sintering |

FIG. 5

DESIGNING AND MANUFACTURING PROSTHETIC IMPLANTS

FIELD OF THE DISCLOSURE

The present disclosure is generally related to prosthetic medical implants, and more particularly to the customization of implants.

BACKGROUND

Attaching medical implants to a patient's anatomy can be logistically difficult and can result in either poor attachments which are prone to displacement, or which can lead to discomfort for the patient. Traditional methods of installing implants require either screws or other mechanical fixtures like bone anchors to hold an implant to a boney structure, adhesives, such as bone cement, or a combination of mechanical and adhesive attachment methods.

While implants can be adapted to a patient's physiology, any customization of the implants generally do not necessarily consider the adhesion sites. This is largely due to the reliance on standardized mechanical attachment methods such as screws. As such, the fitment requires only a generalized fit with efforts at customization focused on the function of the implants and less on optimization of the mating surfaces where the implant meets the boney structures or other parts of the patient anatomy.

Standardized implant components can help to reduce costs and may be sufficient for many applications, however some level of customization is often required. This often requires the fabrication of entire components or assemblies which can prove to be expensive and time consuming.

SUMMARY

This specification discloses systems, methods, and other techniques for creating customized medical implants, including customized implant connectors that are configured to join components of an implant to other components and to the patient's anatomy.

By creating customized connectors to join standardized components, the design and manufacturing of custom parts can be minimized while ensuring adequate fit within the patient. Connectors can additionally be customized to join standardized implant components to a patient's anatomical structures such as bones where the connectors can match the unique physiology. This can prevent displacement of the implant by providing an improved friction fit in addition to any mechanical or adhesive attachment methods used. The choice of materials may additionally improve characteristics of an implant by allowing flexible materials, for example, to be used in connectors, replacing what would otherwise require complex assemblies. Connectors can additionally be customized to reduce or minimize removal of patient tissue, such as bone tissue, which may be drilled, cut, or otherwise removed in the installation of an implant. Connectors may be customized to avoid or reduce contact with sensitive patient tissues, such as nerves, organs, blood vessels or other tissues.

Implementations of the subject matter disclosed herein include methods for customizing connectors for prosthetic implants. The methods can include identifying a prosthetic implant for a patient that can be assembled from multiple implant components. The methods identify that the prosthetic implant requires a connector to secure at least one of the multiple implant components to an anatomical structure of the patient. At least one image of the patient can be acquired depicting an implantation site that includes the anatomical structure of the patient. The at least one image of the patient can be analyzed to determine a profile of the implantation site, the profile including data that characterizes the geometry of a first mating surface of the anatomical structure of the patient. A standardized implant connector can be identified that was designed substantially independent of characteristics of the particular patient. The design of the standardized implant connector can then be modified to generate a design for a customized implant connector that is personalized to the patient. A geometry of a second mating surface for the customized implant can complement the geometry of the first mating surface of the anatomical structure of the patient. A manufacturing subsystem can then be prompted to manufacture a physical instance of the customized implant connector.

These and other implementations can further include none, one or more of the following features.

The prosthetic implant can be or include a hip implant, a knee implant, or a spinal implant.

The prosthetic implant can be implanted in the patient, e.g., using the physical instance of the customized implant connector to secure the at least one of the multiple implant components to the anatomical structure of the patient.

The physical instance of the customized implant connector can be manufactured in situ at the implantation site of the patient.

Prompting the manufacturing subsystem to manufacture the physical instance of the customized implant connector can include selecting one or more manufacturing tools to use in manufacturing the physical instance of the customized implant connector by one or more manufacturing processes. The one or more manufacturing tools can include a three-dimensional (3D) printer and the one or more manufacturing processes can include an additive manufacturing process performed by the 3D printer. Additionally or alternatively, the one or more manufacturing tools can include a computer numerical control (CNC) machining tool and the one or more manufacturing processes can include a subtractive manufacturing process performed by the CNC machining tool.

The design of the customized implant connector can be validated before prompting the manufacturing subsystem to manufacture the physical instance of the customized implant connector. Validation can include simulating use of the customized implant connector to secure at least one of the multiple implant components to an anatomical structure of the patient, obtaining simulation results that include simulated performance metrics for the customized implant connector; and comparing the simulated performance metrics for the customized implant connector to one or more validation criteria to inform a determination whether to reject or accept the design of the customized implant connector.

The simulated performance metrics for the customized implant connector can include at least one of a load metric or a range of motion metric. Comparing the simulated performance metrics for the customized implant connector to the one or more validation criteria can include determining whether a first simulated performance metric falls within an acceptable range for the first simulated performance metric.

In response to a determination that the design of the customized implant connector failed to satisfy at least one of the validation criteria, the design of the customized implant connector can be adjusted. Then, and repeating the simulating, obtaining of simulation results, and comparing of the simulated performance metrics to the one or more validation criteria with respect to the adjusted design of the customized implant connector.

The customized implant connector can be integrally formed in one of the multiple implant components.

The customized implant connector can be a discrete item separate from any of the multiple implant components.

Analyzing the at least one image of the patient to determine a profile of the implantation site can include generating a three-dimensional (3D) model of the implantation site including the anatomical structure of the patient. The geometry of the first mating surface of the anatomical structure of the patient can be derived from the 3D model.

Modifying the design of the standardized implant connector to generate the design for the customized implant connector can include selecting a bio-compatible substrate material from which to manufacture the physical instance of the standardized implant connector.

Modifying the design of the standardized implant connector to generate the design for the customized implant connector can include shaping the customized implant connector to provide an interface for mating with one or more implant components.

Some implementations of the subject matter disclosed in this specification further include a system, one or more computer-readable media (e.g., non-transitory computer-readable media), or both. The system can include one or more processors and one or more computer-readable media having instructions stored thereon that, when executed by the one or more processors, cause the one or more processors to perform any of the foregoing methods or other methods disclosed herein. The computer-readable media can also be encoded with such instructions and provided apart from the one or more processors in additional aspects of the disclosure.

Additional features and advantages will be apparent to one of ordinary skill in the art based upon review of the entire disclosure, including the specification, the figures, and the claims.

BRIEF DESCRIPTION OF THE DRAWINGS

FIG. 3: Illustrates patient data entries in an example patient database.

FIG. 4: Illustrates implant data entries in an example implant database.

FIG. 5: Illustrates substrate data entries in an example substrate database.

Like reference symbols in the various drawings indicate like elements.

The accompanying drawings illustrate various embodiments of the systems, methods, and other aspects of the disclosure. A person of ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1:
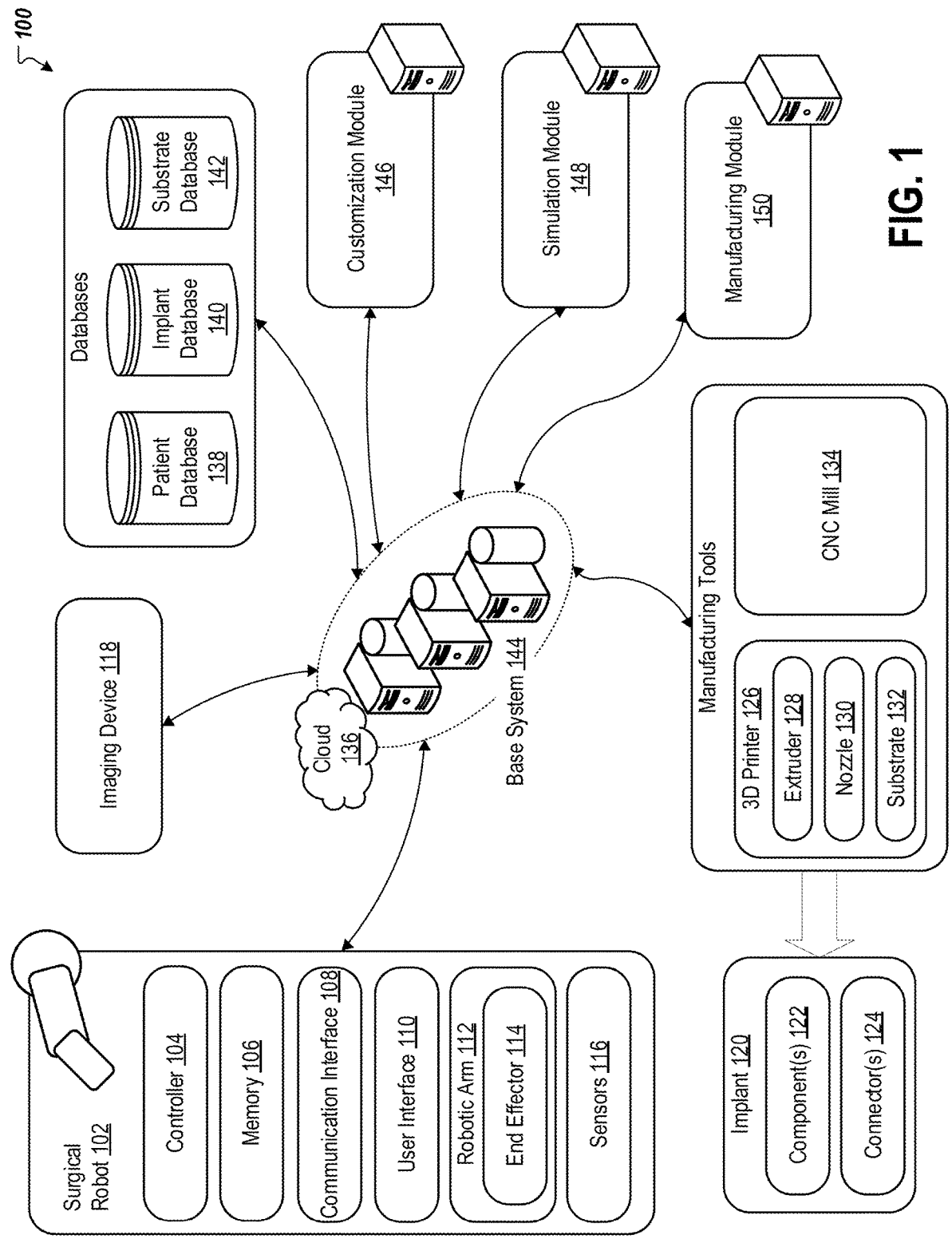
FIG. 1: Illustrates components of an example implant customization system.

FIG. 1 depicts a conceptual diagram of an implant customization system 100. The implant customization system 100 includes a surgical robot 102 configured to assist a surgeon in performing a surgical operation on a patient. A surgical robot 102 may include a controller 104, memory 106, and at least one robotic arm 112 with an end effector 114. The surgical robot 102 may further include a user interface 110 for accepting control inputs from a user, such as a surgeon or other medical professional and a communications interface 108 for transmitting and receiving data to and from a cloud 136 for the purpose of training an artificial intelligence operating within the surgical robot or receiving remote commands from a remote user or an artificial intelligence existing external to the surgical robot 102. The surgical robot 102 may additionally comprise a plurality/of sensors 116 for providing feedback to the user or an artificial intelligence.

A controller 104 is a computing device comprised of one or more processors for performing computations to control operations of the surgical robot 102. Controller 104 communicates with a memory 106 for storing data. The controller 104 is in communication with a communications interface 108 and may further be allowed to control the at least one robotic arm 112 and end effector 114 of a surgical robot 102. The controller may be a commercially available central processing unit (CPU) or graphical processing unit (GPU) or may be a proprietary, purpose-build design. More than one controller 104 may operate in tandem and may be of different types, such as a CPU and a GPU. A GPU is not restricted to only processing graphics or image data and may be used for other computations.

Memory 106 is the electronic circuitry within a computing device that temporarily stores data for usage by the controller 104. The memory 106 may additionally comprise persistent data storage for storing data used by the controller 104. The memory 106 may be integrated into a controller 104 or may be a discrete component. The memory 106 may be integrated into a circuit, such as soldered on component of a single board computer (SBC) or may a removable component such as a discrete dynamic random-access memory (DRAM) stick, secure digital (SD) card, flash drive, solid state drive (SSD), magnetic hard disk drive (SSD), etc. In some embodiments, memory 106 may be part of a controller 104. Multiple types of memory 106 may be used by the surgical robot 102.

A communication interface 108 allows the surgical robot 102 to communicate with external devices and may comprise a wireless antenna and transceiver or a port for receiving a cable to facilitate a wired connection. Examples of a wired connection include ethernet, universal serial bus (USB) or a proprietary connection. A wireless communication interface 108 may include any of Wi-Fi, Bluetooth, near field communications (NFC) or a cellular communications interface such as 3G, 4G, LTE, or 5G. The communications interface 108 may connect a user interface 110 to the surgical robot 102 or may facilitate access to a local network or a cloud 136 network to access a remote server and/or database.

A user interface 110 provides functionality for interacting with a surgical robot 102 and may include any of a keyboard, computer mouse, trackball, joystick, wireless or wired gamepad, sliders, scroll wheels, touch screen or microphone for receiving voice commands. The user interface 110 may additionally include any method of interaction of a user with a surgical robot 102 not listed. The user interface 110 may accept direct inputs, such as from a joystick controlling the movement of a robotic arm or indirect inputs such as commands entered on a keyboard or touch screen such as adjusting the sensitivity of a joystick control or the speed of a robotic arm's 112 movement in response to a joystick. The user interface 110 may also comprise a screen for presenting information to the user such as patient status, imaging data, and navigation data and speakers for providing auditory feedback. The user interface 110 may also utilize haptics to provide feedback to the user. A user interface 110 may also be used to interact with and control a system for designing, modifying, and manufacturing an implant 120, implant components 122, and connectors 124.

A robotic arm 112 is a mechanically actuated arm or lever with at least two degrees of freedom. A robotic arm 112 will typically include at least one end effector 114 or an imaging device 118 and may include both an end effector 114 and an imaging device 118. The robotic arm 112 may additionally be capable of changing the end effector 114 to facilitate multiple functions and operation of a variety of tools. The robotic arm 112 may be manually controlled or operated in an autonomous or semi-autonomous mode. A surgical robot 102 may have one robotic arm 112 or multiple robotic arms 112, each of which may be operated independently by one or more users or autonomous systems or a combination of users and autonomous systems. A robotic arm 112 may additionally be comprised of components to facilitate the operation of one or more end effectors 114 such as a communication interface 108 for providing instructions to the end effector 114 and a source of electrical and mechanical power for use by an end effector 114. Additionally, a hopper, reservoir, feeder, etc. for a substrate 132 for use in a 3D printer 126 which may be used as an end effector 114 or in place of an end effector 114 may be integrated into a robotic arm 112 to enable in situ 3D printing of a connector 124 or other implant component 122. An end effector 114 is the end of a robotic arm 112 which is conducting work.

The end effector 114 is typically a tool or device for interacting with a physical object and may be a surgical tool intended for acting upon or within a patient or may be a gripping device for securing a separate surgical tool to a robotic arm 112. The end effector 114 may be permanently affixed to the end of a robotic arm 112 or may be detachable allowing for a system of interchangeable end effectors 114 which may alternatively be selected and swapped by a single robotic arm 112 or multiple robotic arms 112. In some embodiments, an end effector 114 may be a 3D printer 126 or a nozzle 130 used to extrude a substrate 132 for use in a 3D printing operation.

A sensor 116 is a measurement tool for monitoring a characteristic or metric associated with a surgical robot 102, end effector 114 or patient. A sensor 116 may be discrete or part of an array or assembly, such as force transducers integrated into an end effector 114 to monitor the forces applied to the patient. One or more of the sensors 116 may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc. The sensors 116 may be integrated into the operation of the surgical robot 102 or may monitor the status of a patient. The data acquired by the sensors 116 may be used to train a machine learning model used by the surgical robot 102 or artificial intelligence to control the surgical robot 102.

An imaging device 118 refers to any device capable of collecting data which can be used to create an image, or a representation of a physical structure or phenomena. An imaging device 118 may include any device capable of detecting sound or electromagnetic waves and assembling a visual representation of the detected waves. Imaging devices 118 may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device 118 may be interpolated from direct measurements representing adjacent pixels in order to increase the resolution of a generated image. The system may receive or generate imaging data from a plurality of imagining devices 118. The plurality of imaging devices 118 may include, for example, cameras attached to the robotic arm 112, cameras mounted to the ceiling or other structures above or otherwise in view of the surgical theater, cameras that may be mounted on a tripod or other independent mounting device, cameras that may be body worn by the surgeon or other surgical staff, cameras that may be incorporated into a wearable device, such as an augmented reality device like GOOGLE GLASS, MICROSOFT HOLOLENS, etc., cameras that may be integrated into an endoscopic, microscopic, laparoscopic, or any camera or other imaging devices 118 (e.g. ultrasound) that may be present in the surgical theater. The imaging device 118 may include any algorithm or software module capable of determining qualitative or quantitative data from medical images, which may include, for example, a deep learning algorithm that has been trained on a data set of medical images. An imaging device 118 may further refer to a device used to acquire medical imagery by any means including magnetic resonance imaging (MRI), computed tomography (CT), X-Ray, positron emission tomography (PET), ultrasound, arthrography, angiography, myelography, etc.

Implant 120 is a structure or a collection of related structures configured to be embedded within the body of a patient. The implant 120 can include one or more implant components 122. An implant 120 may additionally include one or more connectors 124, which are adapted to mate two or more implant components 124 to each other or to join one or more implant components to a tissue structure in a patient. The implant 120 may be rigid, flexible, or may include both rigid and flexible components. The implant 120 may be made of synthetic materials such as biocompatible metals, metal alloys, plastics, resins, ceramics, The implant 120 can further or alternatively include organic materials such as tissues harvested or derived from humans or animals. In some embodiments, an implant 120 may comprise both organic and inorganic implant components 122.

Implants 120 may be customized to fit a patient's unique physiology or a specific function. Implants 120 may provide reinforcement to a patient's physiology or may replace, repair, or improve the function or performance of a part of the patient's body, such as replacing a knee joint or inserting a stent to open a vein or block off an aneurism. An implant 120 may also be prosthetic or therapeutic devices which are attached to the patient's body. An implant 120 is characterized by being surgically attached to the patient, however the entirety of the implant 120 does need to be fully embedded within the patient and part or all of the implant 120 may be exposed even after patient recovery. In such cases, implant 120 and implant components 122 will relate to parts of such implants 120 which contact the patient. An implant component 122 is a discrete component or sub-assembly of an implant 120 when the implant 120 has multiple components or sub-assemblies.

An implant component 122 can be made in whole or in part using biocompatible material(s) that do not illicit an immune response from the patient when implanted. Biocompatible materials may be organic or inorganic. Examples of inorganic biocompatible materials include metals, such as titanium, metal alloys such as titanium alloys, stainless steel, and cobalt-chromium alloy, ceramics such as zirconia and bioglass, thermoplastics such as polyvinylchloride (PVC), polyethylene (PE), polypropylene (PP), polytetrafluoroethylene (PTFE), and polymethylmethacrylate (PMMA), and other resins and materials including alumina, hydroxyapatite, medical-grade silicone, trimethyl carbonate, TMC NAD-lactide, etc.

Implant components 122 can further include organic structures such as organs harvested from human or animal donors or tissues and compounds which may be grown or otherwise synthesized in a lab. An implant 120 may be comprised of a single implant component 122. Implant components 122 may be customizable.

An implant component 122 may additionally comprise one or more connectors 124 or be designed to mate with at least one connector 124. A connector 124 can be a part of an implant component 122 that is designed to mate with at least one implant component 122 or the physiology of a patient. A connector 124 may be integrated into a part of an implant component 122 or may be a standalone component. A connector 124 may be standardized or customized to meet a specific purpose, such as a unique dimension, orientation, or functional purpose. A connector 124 may comprise a rigid structure or may be a flexible structure due to a mechanical design or the physical properties of the substrate 132 comprising the connector 124. A connector 124 may join two or more implant components 122 or may alternatively join one or more implant components to tissues structures of a patient, such as to a patient's bone. A connector 124 may comprise a single component or may comprise several components, such as a mating surface or plate and one or more screws which may be used to secure an implant 120 to tissue structures within a patient. In such an example, each component could be individually referred to as a connector or the assembly of multiple parts may comprise the connector 124.

A 3D printer 126 is comprised of at least an extruder 128, nozzle 130 and a supply of substrate 132. Substrate 132 is drawn from a supply, which may be one or more of reservoirs, a spool of filament, a hopper of raw pellets, etc. by at least one extruder 128. The extruder 128 then forces the substrate 132 through a nozzle which deposits a controlled amount of substrate 132 onto the print site. The 3D printer 126 may be capable of depositing material at any orientation. The 3D printer 126 may be a stand-alone machine or may be integrated into an end effector 114 of a surgical robot 102. The 3D printer 126 may store the substrate 132 externally and may feed the substrate to a print head comprising at least the nozzle 130, via a conduit which may be run along or through at least part of a robotic arm 112. The 3D printer 126 may print using methods such as fused filament fabrication (FFF), fused deposition modeling (FDM), stereolithography (SLA), selective laser sintering (SLS), digital light process (DLP), multi jet fusion (MJF), direct metal laser sintering (DMLS), electron beam melting (EBM), etc.

The 3D printer 126 may use additive manufacturing techniques such as welding or soldering to manufacture an implant component 122 or connector 124

Extruder 128 is a component of a 3D printer which receives substrate 132 from a reservoir, spool, hopper, etc. and advances the substrate 132 through a nozzle 130. The extruder 128 controls the rate of flow of the substrate 132 through the nozzle 130. In some embodiments, the extruder 128 may also function as a mixer to combined or agitate one or more substrates 132. For example, a substrate 132 comprising a two-part resin epoxy may be combined and mixed by the extruder 128 prior to being advanced to the nozzle 130. In some embodiments, a mixer, if required, may be a separate component which may combine or agitate the one or more substrates 132 prior to being received by the extruder 128. In some embodiments, multiple extruders 128 may be utilized, with one being positioned between a supply of substrate 132 and a mixer and a second being positioned between the mixer and the nozzle 130. Further embodiments may include a plurality of extruders 128 each paired with a nozzle 130. Multiple substrates 132 may be combined to achieve a desired material property or to activate a desired chemical reaction. Multiple substrates 132 may alternatively be used in succession to achieve a composite component comprised of different materials, each with their own physical properties. In some embodiments, an extruder 128 is a pump. In some embodiments, an extruder 128 may additionally comprise or accompany a hot end for heating a substrate 132. In some embodiments, an extruder 128 may comprise a mechanism for moving a print bed and facilitating the movement of loose or uncured substrate 132 over the object being printed such as in SLA and SLS 3D printers 126.

The nozzle 130 provides an orifice through which substrate 132 is flowed and deposited on a print surface. A print surface may be a print bed or plate of a 3D printer 126 or may be a prepared surface comprised of a patient's tissues, a synthetic surface, such as one or more implant components 122, one or more connectors 124, or on a previous layer of extruded substrate 132 including any material which may be applied to form an adhesion layer to promote adhesion of the substrate 132 to a base material such as the patient's tissues including bone, skin, muscle, fascia, tendons, ligaments, blood vessels, etc. or a print bed or plate. The nozzle 130 may be cast or machined from metal or plastic as a single piece or may comprise multiple components. In some embodiments the nozzle 130 may be capable of dynamically increasing or decreasing the orifice size and may additionally be capable of articulating to achieve a range of orientations independent of movement by the robotic arm 112. The nozzle 130 may also comprise multiple orifices or alternatively multiple nozzles 130 may be supplied by one extruder 128.

A substrate 132 is a material which is dispensed by a 3D printer 126. A substrate 132 may be dispensed as a liquid which may be heated, mixed, or otherwise prepared to be applied via an extruder 128 and nozzle 130. A substrate 132 may alternatively be dispensed as a solid, powder or gas. A substrate 132 may alternatively reside in a reservoir, vat, etc. into which a build plate may be lowered such as in some SLA 3D printers 126. A substrate 132 may be capable of bonding to the patient's tissues, synthetic surfaces, the same substrate 132 or other substrates 132. A substrate 132 may adhere temporarily to a build plate with or without preparation, such as the application of an adhesion material or layer.

The substrate 132 may be chosen for any number of physical properties including the types of surfaces or materials to which it will or will not readily adhere to. Special adhesive materials may be applied or dispensed to promote adhesion between a print surface and the substrate 132. Such materials may include adhesives such as glues and may be applied via the 3D printer 126 or other means. Substrate 132 can include all such adhesive materials. A substrate 132 for use within a living body can be biocompatible, possessing the properties of being non-toxic and should not illicit a rejection response by the body. Such properties may be specific to a patient such as in the case of a patient having an allergy or sensitivity to a material. Examples of biocompatible substrates 132 include alumina, bioglass, cobalt-chromium alloy, hydroxyapatite, medical-grade silicone, polyvinylchloride (PVC), polyethylene (PE), polypropylene (PP), polytetrafluoroethylene (PTFE), polymethylmethacrylate (PMMA), stainless steel, trimethyl carbonate, TMC NAD-lactide, titanium and titanium alloys, zirconia, etc. A substrate 132 may include a thermoplastic, preferably with a low melting point. When thermoplastics are used, a hot end may be positioned between the extruder 128 and the nozzle 130. In alternate embodiments, metals may be used as a powder or mixed with a binder such as in a filament or resin and may additionally use a laser sintering process to bond the material. In further embodiments, a resin may be used which may require the mixing of a first part and a second part to initiate a chemical reaction which causes the combined material to harden. Either part of a two-part resin may be a liquid or a pliable solid such as a resin clay material. Additional additives may be mixed with a traditional two-part resin to achieve the desired physical properties. Some resins may cure when subjected to a UV light. In such embodiments, a UV light source may be affixed to or integrated into the 3D printer 126, end effector 114 or nozzle 130 or may otherwise be present to cure the substrate 132 deposited by the 3D printer 126. A substrate 132 may also include any raw material used to manufacture an implant component 122 or connector 124 such as an ingot of metal.

A CNC mill 134 is a method of subtractive manufacturing which removes materials using a rotating tool such as a bit or end mill. The rotating tool may move in two spatial dimensions (e.g., horizontally along X- and Y-axes), and optionally may further move in a third dimension (e.g. vertically in a Z-axis). In some embodiments, a CNC mill 134 may move the rotating component in one or more rotational axes. The CNC mill 134 may use a plurality of interchangeable bits or other tooling to facilitate the removal of material. A CNC mill 134 may create an implant component 122 or connector 124 by removing material from a source substrate 132 such as an ingot. A CNC mill 134 may alternatively be used to remove material from a 3D printed implant component 122 or connector 124. In some embodiments, a CNC mill 134 removes material or substrate 132 during the manufacture of an implant component 122 or connector 124.

Cloud 136 includes a distributed network of computers that provide online services at one or more locations proximate to and/or remote from the surgical site. Cloud 136 may be a private cloud 136 in which access is restricted to authorized users. Alternatively, cloud 136 may be a public cloud 136 in which access is widely available via the Internet. A public cloud 136 may not be secured or may include relatively limited security features.

Cloud 136 may include one or more servers and one or more databases, e.g., patient database 138, implant database 140, and substrate database 142. Patient database 138 stores patient data including electronic medical records, diagnosed conditions, patient specific baseline values, such as heart rate, blood pressure, etc. and medical imaging data. The patient database 138 may additionally comprise personal identity information for patients, insurance and billing information for patients, personal contact information for patients, and emergency contact information for patients. The patient database 138 may also store records of legal documentation such as executed consent forms that patients have signed to provide authority for medical professionals to perform one or more procedures on the patient. The patient database 138 may further store data indicating familial relationships and genetic data to facilitate a comprehensive family history for individual patients.

In some embodiments, patient database 138 stores medical images which may be used by a customization module 146 or simulation module 148 to determine aspects of the patient's anatomy which may affect the design of the implant 120, implant components 122, and/or connectors 124. Medical images may additionally include annotations from a practitioner and/or algorithm which may identify one or more tissue types, structures, and/or other anatomical features depicted in the image. The medical images and annotations may be used by the customization module 146 or simulation module 148 to affect the design and construction of the implant 120, implant components 122, or connectors 124.

Implant database 140 stores about one or more implants 120. This data can indicate the type of implant 120, location where the implant 120 is installed, the number and type of implant components 122 and connectors 124 and specific properties of the implant components 122 and connectors 124 including dimensions, materials, manufacturing methods, and may additionally include physical characteristics including hardness, flexibility, etc. The implant database 140 may additionally store data about the procedures used to install the implants 120, patient information about the patients in whom the implants 120 are installed, and patient outcomes. The implant database 140 may be populated by a separate system which may customize the implant 120, implant components 122, or connectors 124 or a database such as a third-party source which may include the manufacturer of an implant 120, implant components 122, or connectors 124.

Substrate database 142 stores data about 3D printer 126 substrates 132 such as physical properties of printed substrate material, physical properties of material prior to extrusion, actions required for extruding the substrate 132 such as mixing or heating, requirements for curing, such as environmental conditions and time, and the materials with which it will or will not readily bond. Substrate database 142 can further include data indicating materials and corresponding physical properties which are not intended to be used as substrates 132 such as materials which may be toxic or which may illicit a rejection response by the body. Such materials may also include body tissues such as bone, muscle, fascia, skin, etc.

Base system 144 uses at least one imaging device 118 to acquire one or more images of a patient, specifically images of the surgical site where the implant 120 is to be installed. Customization module 146 is invoked and receives image data and queries the implant database 140. An implant 120 design is selected and a list of implant components 122 is identified. From the list of implant components 122, standardized implant components 122 are selected which are suitable for use in the implant 120 and connectors 124 are designed to mate the standardized implant components 122 to one another or to an anatomical feature of the patient. The present techniques can reduce cost and improve availability of implant components 122 by using primarily standardized parts and mating the standardized implant components 122 using custom connectors to match the geometry formed by the standardized implant components 122. The limited number of customized implant components 122 can also decrease the amount of time required to manufacture the custom implant components 122, e.g., thereby making it practical to perform customizations in a hospital setting instead of relying on implant components 122 being customized in a traditional manufacturing setting. In additional embodiments, the implant components 122 can be customized to form customized interfaces with parts of the body such that the implant component 122 is optimized for fit, increasing the surface area which contacts the patient's physiology, or alternatively matching the contours of the patient's body. These customizations may be based upon medical imagery of the patient's body prior to the implant 120 installation process during a planning process during which a custom connector 124 may be designed, simulated, and adjusted. When all of the necessary connectors 124 have been designed, data characterizing the customized implant 120, implant components 122, and connectors 124 are communicated to the base system 144, and simulation module 148 is invoked.

Simulation module 148 receives data characterizing implant components 122 and connectors 124, and using such data, simulates the interactions of the implant components 122 and connectors 124 using methods such as finite element analysis (FEA) tools, and other techniques that might be applied to validate a 3D model. The simulations may include dynamic operations such as installation procedures, and the operation of the assembled implant 120 in the patient including load, flexibility, and evaluation of other metrics. The simulations may additionally utilize patient data to predict the patient's range of motion, maximum load, reaction speed, etc. before and after the installation of the implant 120 to determine if the expected range of motion and other performance characteristics of the implant 120 will meet the lifestyle requirements of the patient. This is of particular importance for designing, testing, manufacturing and installing implants 120 in athletes or professionals in physically demanding professionals to ensure such a procedure does not adversely affect their career performance. For example, the forces on a pedicle screw may be calculated with respect to the patient, the location on the spine, and parameters indicative of the patient's lifestyle (e.g., active or sedentary) to develop a more robust simulation from which an optimized implant design can be determined. If the connectors 124 do not perform within specified tolerance ranges, an error may be logged. The simulation results (and any logged errors) are then communicated to the base system 144.

Using the simulation results, base system 144 determines whether modifications to the implant 120, implant components 122, or connectors 124 are required, and if so, invokes the customization module 146 and provides logged errors and any other data received from the simulation module 148 to the customization module 146 (which in turn uses the data to implement the modifications). If modifications are not required, the system invokes manufacturing module 150 to begin manufacturing implant 120 including components 122 and connectors 124.

Upon receiving a final design for implant components 122 and connectors 124, manufacturing module 150 commences manufacturing. Manufacturing module 150 can query the substrate database 142, select a tool, and initiate a manufacturing process such as an additive or subtractive manufacturing process. Manufacturing processes are performed until the connector 124 is complete and then repeated for all connectors 124. The connectors 124 are then received by the base system 144 and the implant components 122 and connectors 124 are installed in the patient. The customization module 146 receives image data acquired from at least one imaging device 118 from the base system 144 and queries the implant database 140 for implant 120 designs. An implant 120 design is selected and a list of implant components 122 is identified. The implant components 122 may additionally comprise connectors 124 for joining the plurality of implant components 122 and further joining the completed implant 120 to the patient's physiology. Standardized implant components 122 are identified and the remaining implant components 122 including connectors 124 are designed. Each implant component 122 and connector 124 is saved to the implant database 140 and the implant components 122 and connectors 124 are sent to the base system 144.

The simulation module 148 receives data characterizing implant components 122, connectors 124, and image data from the base system 144. Simulation module 148 performs simulations to analyze the interactions between implant components 122, particularly focusing on the performance of the connectors 124 in simulated use. The simulations may include simulating assembly of the implant components 122 and connectors 124, including simulating the installation procedure and the fit of the components 122 and connectors 124. Simulations can also be used to assess the performance of implant components 122 and connectors 124, including assessing the flexibility and ability of the components 122 and connectors 124 to handle a load. The simulations may be used to test the durability of the implant components 122 and connectors 124. The simulation results including any issues which may be saved in an error log may be saved to the implant database 140 and communicated to the base system 144.

Manufacturing module 150 receives data characterizing implant component 122 and connector 124 designs from the base system 144. Manufacturing module 150 queries substrate database 142 for material parameters for the substrates 132 to be used in the manufacture of the implant components 122 and connectors 124. The material parameters may include indications of the type of manufacturing operation to be employed in constructing the implant 120 with the specified materials (e.g., additive or subtractive manufacturing methods), as well as the parameters for each manufacturing method, such as heat, flow rate, print rate, cure time, etc. for a thermoplastic or resin 3D printer 126 or tooling, spindle speed, feed rate, etc. for a CNC mill 134. For each implant component 122 or connector 124 being manufactured or modified, the system may select a manufacturing tool, and may perform a manufacturing operation, which may be an additive process such as by a 3D printer 126 or a subtractive process such as by a CNC mill 134. Upon completion of the manufacture of each implant component 122 and connector 124, the process initiates manufacture of the next component 122 or connector 124 until all requested components 122 and connectors 124 have been manufactured. The implant 120 can be implanted in the patient using the manufactured component(s) 122 and connector(s) 124.

Figure 2:
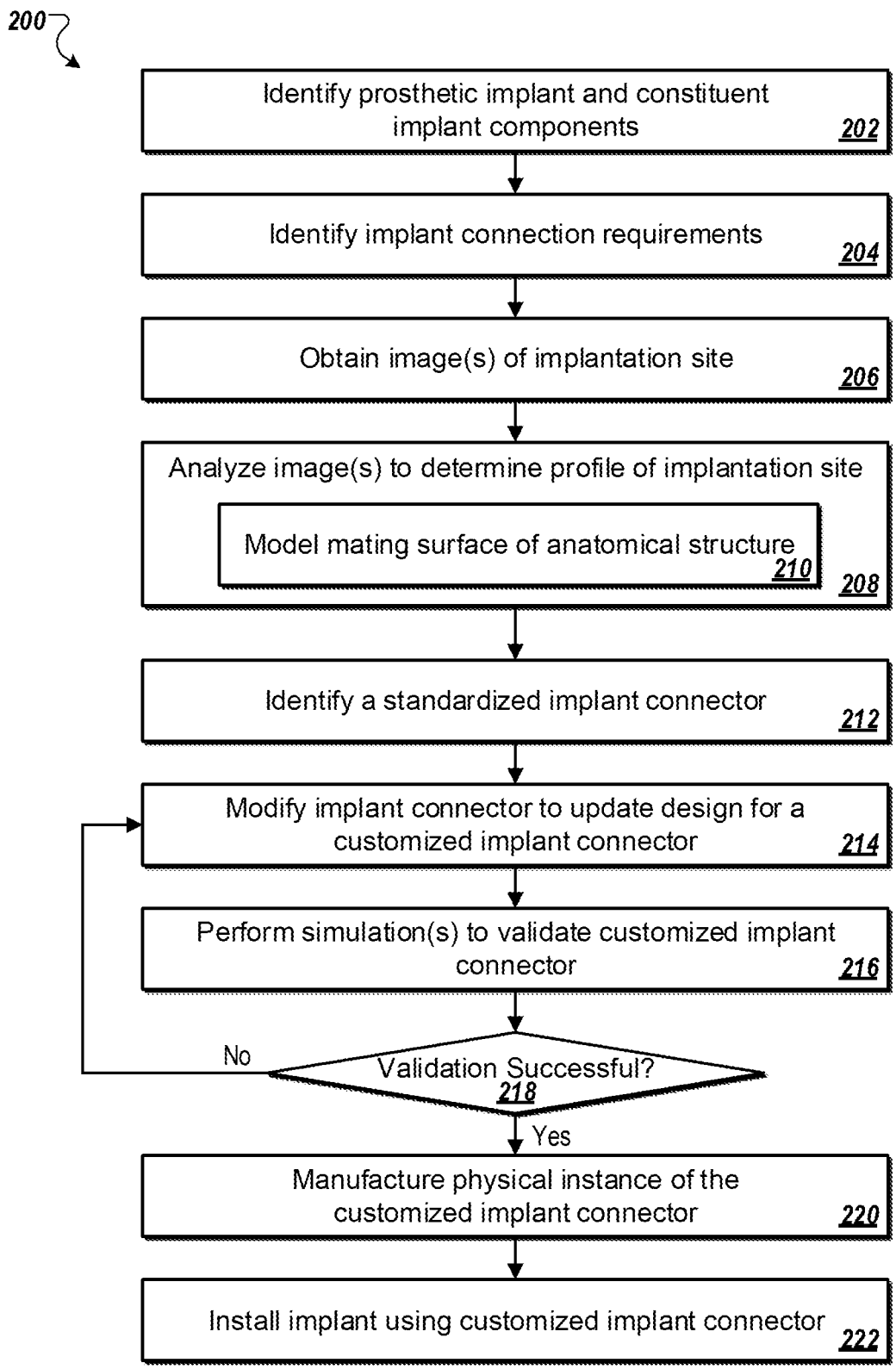
FIG. 2: Illustrates an example process for designing a custom implant connector.

FIG. 2 shows a flowchart of an example process 200 for designing, manufacturing, and installing a prosthetic implant 120 having customized connectors 124. The process 200 may be carried out by an implant customization system like the system 100 described with reference to FIG. 1. Notably, while the description of FIG. 2 focuses on the customization of an implant connector 124 to mate with an anatomical structure of a patient, the process 200 can be readily applied to customize a connector 124 to join two or more implant components 122 (e.g., by customizing the interface of the connector 124 to have a complementary geometry to the respective interfaces of the joined implant components 122). Similarly, process 200 can be applied to customize an interface component 122 to accommodate other standard or customized components 122, implant connectors 124, the unique physiology of the patient, or a combination of such options.

The process 200 can begin by identifying a prosthetic implant 120 that is to be prepared for implantation in a patient (202). The implant 120 can include a set of implant components 122, which can be assembled to form the implant 120. Furthermore, for each junction between a component 122 and another component 122 or between a component 122 and the patient's anatomy, a connector 124 can be provided to implement the junction between the component 122 and other component(s) 122 or between the component 122 and the patient's anatomy. The implant 120 and its components 122 can be identified from an implant database such as implant database 140. For example, the system may access an electronic medical record (EMR) for the patient from a patient database (e.g., patient database 138). The patient's EMR may reference an implant 120 that is to be installed in the patient in an upcoming procedure, and the system may then look up details about the referenced implant 120 in a separate implant database 120. In some embodiments, the implant database explicitly identifies each of the components 122 and connectors 124 that are needed to assemble and install the implant 120 in the patient, and in this case, the system can identify the required connectors 124 directly from the implant database itself (204). In some embodiments, the implant customization system may identify where junctions exist in the implant 120 between different components 122 or between components 122 and the patient's anatomy, and the system may use this information to dynamically identify where connectors 124 are needed to facilitate assembly and implantation of the implant 120.

For example, for a hip implant 120, the implant components 122 may include at least a socket to be affixed to the patient's pelvis which may be comprised of several segments which may be attached to each other and have multiple attachment points to the patient's pelvis. The hip implant 120 additionally can include a ball portion to be affixed to the patient's femur and designed to be captured by the socket attached to the pelvis. Connectors 124 can be used to join segments of the socket component 122 to each other, and to secure each of the socket component and the ball portion component to the pelvis and the femur, respectively. Likewise, a knee implant 120 may comprise a hinge which may include at least a first plate, for mounting to the patient's femur, a second plate for mounting to the patient's tibia, and a pin or other connector 124 for joining the first and second plates. A spinal implant 120 may include a plurality of rods, plates, screws, and other connectors 124.

The patient can further undergo one or more imaging procedures to acquire one or more images of the implantation site, i.e., the area of the patient's body where the implant is planned to be installed. Images can be acquired with an imaging device like those described with respect to imaging device 118. In some embodiments, the system acquires images using magnetic resonance imaging (MRI), computed tomography (CT), X-Ray, positron emission tomography (PET), ultrasound, arthrography, angiography, or myelography. In some embodiments, the acquired images focus on particular anatomical structures to which the implant 120 will be anchored. For example, considering a hip implant 120, the imaging device 118 may acquire images of the pelvic area of the patient, and more specifically, images of the pelvic bone and the femur in the areas where the socket and ball components 122 of the implant 122 are to be attached.

Images of the implantation site are analyzed to generate a profile of the implantation site (208). The profile characterizes information about the implantation site that can be used to assist the surgeon in preparing and carrying out an implantation procedure, that can be used by customization module 146 to design customized components and connectors tailored to the patient's unique physiology, and that can be used by simulation module 148 to render virtual representations/simulations of the implantation site and to determine appropriate validation criteria for customized component and connector designs. In some embodiments, the profile (which can be maintained in the patient database 138, for example) stores the acquired images of the implantation site. In some embodiments, the profile stores values for measured properties of the implantation site that have been derived from the images and/or other sources, such as dimensions of anatomical structures of the patient in the implantation site and conditions of anatomical structures in the implantation site (e.g., bone density, lesion information). The measured properties can be determined using an image analyzer module (not shown), which is in turn configured to run one or more image analysis routines on the images using object detect, object recognition, and/or machine-learning techniques. Manual image inspection can also be performed to obtain data for the profile of the implantation site.

In some embodiments, the system includes a modeling engine that generates a three-dimensional (3D) model of the implantations site, or of particular anatomical structures in the implantation site, from the acquired images of the patient (210). Any suitable technique can be used to generate the 3D model, which may include solid modeling, wireframe modeling, surface modeling, or other techniques or combinations of techniques. As an example, a 3D model may be created from a sequence of images obtained of an implantation site using magnetic resonance imaging (MRI). Each image in the sequence can represent a 2D slice of the implantation site, where each slice is acquired at a different location along an axis orthogonal to the 2D slice. Corresponding points or features in the images can be traced from slice to slice, and a 3D model built by determining 3D coordinates for the surfaces or outlines of anatomical structures based on their position in the 2D slices and the known distance between each slice. The 3D model can aid the system in customizing implant components 122 and connectors 124, and in generating meaningful simulations that accurately portray the implantation site.

To develop a customized connector 124, the system first selects a standard implant connector as a starting point for the design of the customized connector 124 (212). The standard implant connector provides a baseline or a template for the customized connector 124, and defines a design for a generic, non-customized version of a connector for a particular junction of a particular implant. Standard implant connectors can be stored in the form of a 3D model, such as a computer-aided design (CAD) file, or in other suitable formats. In some embodiments, implant database 140 stores a library of standardized connectors. Different models in the library can represent different types of standardized connectors, and in some cases, the library can different models for variants of each type of connector. For example, the library may store standard models of spinal implant connectors, knee implant connectors, pelvic implant connectors, and more. Different standardized connectors can be defined for each junction in each implant, and in some cases, different variants of standardized connectors can be defined for each type of connector (e.g., to accommodate different sizes or loads required to be borne by the connector). Customization module 146 can select an appropriate standardized connector from the library by identifying the particular junction for which a connector is needed in the implant 120, and querying implant database 140 to identify the standardized connector associated with the particular junction.

The customization module 146 uses the design of the standardized connector to create a customized design for a customized connector 124 (214). In some embodiments, customization module 146 loads a model of the standardized connector, and then applies a set of transformations or modifications to the standardized connector to customize it for use in a particular application with a particular patient. For example, customization module 146 may adjust one or more dimensions of the standardized connector based on the needs of the patient, may add or remove structural reinforcements or other features to the standardized connector to ensure the connector can bear an appropriate load for the patient, may select a suitable substrate or other material from which to form the connector based on the needs of the patient, or may apply multiple such adjustments. In some embodiments, the customization module 146 specifically targets customization of the adhesion sites where the connector will mate with a boney structure or other anatomy of the patient. The adhesion sites may be sized and shaped to precisely match the contours of the planned attachment points (adhesion sites) of the patient's anatomical structures (e.g., bone surfaces). In some cases, the degree of customization applied to different portions of the connector can vary as a function of distance from the adhesion site. Tighter tolerances may be applied to the actual adhesion sites than non-adhesion sites, such that the adhesion sites of the connector will more closely match the contours of the patient's anatomy than non-adhesion sites. The resulting model of the customized connector 124 can be stored in implant database 140 for subsequent access. Additional detail regarding operation of the customization module 146 is described with respect to FIG. 7.

Before the customized connector 124 is made available for production, it must in some embodiments be validated to ensure it meets certain safety and performance specifications (216). To validate a proposed design for a customized connector 124 (or customized implant component 122), the system can provide the proposed design to a simulation module 148. Simulation module 148 simulates the performance of the customized connector 124, and uses the simulations to perform one or more tests on the proposed design. In some examples, the tests include structural tests that assess the strength of customized connector 124 across the entire device. This can be accomplished using finite element analysis (FEA) or other suitable techniques. In some examples, the system tests interactions between the customized connector 124 and other implant components 122, the patient's anatomy, or both. For instance, simulation module 148 may run simulations that involve weight loading, range of motion, endurance, etc. to verify whether the proposed design of the customized connector 124 is suitable for use in a real patient. Simulation results can be obtained and compared to validation thresholds or other criteria to determine whether connector 124 is validated. Additional detail regarding validation and operation of the simulation module 148 is described with respect to FIGS. 6 and 8.

If validation was successful (218), the process 200 releases the design of the customized connector 124 for production. In this case, a physical instance of the connector 124 can be manufactured under the direction of a manufacturing module 150 using one or more manufacturing tools such as a 3D printer 126 for additive manufacturing, a CNC mill 134 for subtractive manufacturing, or combinations of manufacturing techniques (220). In some embodiments, the manufacturing tools are provided on a robotic arm 112 of a surgical robot 102, which allows the connector 124 to be produced on site during or in preparation for an implant procedure on a patient. The implant 120 is then implanted in the patient, and assembled using one or more customized connectors 124 (222). Additional detail regarding operation of the manufacturing module is described with respect to FIG. 9.

In some cases, the system iteratively refines and re-simulates proposed designs of the customized connector 124 until a satisfactory design is achieved that meets all the requisite validation criteria. Thus, if validation was not successful for the proposed design in the first instance (218), the process 200 can return to (214), and further modify the design of the connector 124 with the aim of making the connector 124 compliant with all requisite validation criteria. Once the refined design is completed by the customization module 146, the design is provided for a new round of simulations by simulation module 148. The simulation module 148 again compares the simulation results to pre-defined validation criteria, and determines whether additional refinements to the design are needed, or if the current iteration of the design can be released for manufacturing.

FIG. 3 depicts entries in an example patient database, e.g., patient database 138. The patient database 138 stores data about one or more patients and may include electronic medical records. A patient database 138 may include personally identifiable information, such as, for each patient, the name, date of birth, address, and insurance information for the patient. Patient database 138 may further include information about a patient's health or medical history such as diagnosed conditions, allergies, medications, normal baseline vital sign ranges for the patient, etc. The patient database 138 may be populated by medical professionals such as a patient's physician, specialists such as surgeons, therapists or any other medical professionals including nurses, emergency medical technicians, paramedics, etc. The patient database 138 additionally stores images acquired by the base system 144 using at least one imaging device 118 and may additionally store data related to the patient from the customization module 146 and simulation module 148.

The patient database 138 is used by the base system 144, customization module 146, and simulation module 148. The patient database 138 may include, for example, medical images produced by imaging device 118, which may be, for example, X-rays, CT (computed tomography) scan, positron emission tomography (PET) scan, MRI (magnetic resonance imaging), ultrasound, nuclear medicine imaging, including positron-emission tomography (PET). Medical images may further comprise still images or videos from a camera either external or internal to the patient, such as an endoscope, laparoscope, etc. Medical image data may include metadata from the images, such as the specific model of equipment used to generate the image, the date and time the image was captured, the geographic location of the image, the anatomical location of the image, the practitioner(s) who performed the imaging, etc. Additionally, the medical image data may include annotations from a practitioner and/or algorithm which may indicate tissue types, structures, and/or other anatomical features.

The patient database 138 may further store 3D anatomical models/representations of patient tissue at a targeted implant site. The 3D models can be derived from medical images of the targeted implant site. For example, the system can use cross-sectional imaging data from an MRI device to convert pixels from individual cross-sections into voxels defining a 3D volume by extrapolating the volume between corresponding pixels of at least two medical images. The volume may be determined by the distance between cross-sections that the MRI machine generated. The 3D anatomical model/representation may further be generated by combining cross-sectional images from two or more axial planes of an imaging modality, such as an MRI. In one example, patient database 138 stores an MRI scan of a male patient, age 46. The MRI may show portions of the hip joint which need to be replaced with prosthetic implants. The patient data for this patient may also include a prescription for the removal and replacement of portions of the pelvis and femur that form the patient's hip joint. The patient database 138 may further store or reference a 3D model of the patient's hip joint and the prosthetic that needs to be implanted.

FIG. 4 depicts entries in an example implant database, e.g., implant database 140. The implant database 140 stores implant data that indicates a range of information about implants 120, implant components 122, and connectors 124. Implant data can include data indicating, for each implant 120, a type of the implant 120, a location of the implant 120, one or more constituent components 122 of the implant 120, the material(s) of each implant component 122, and the properties of those materials. For example, the implant 120 materials may comprise one or more of any biocompatible material including alumina, bioglass, cobalt-chromium alloy, hydroxyapatite, medical-grade silicone, polyvinylchloride (PVC), polyethylene (PE), polypropylene (PP), polytetrafluoroethylene (PTFE), polymethylmethacrylate (PMMA), stainless steel, trimethyl carbonate, TMC NAD-lactide, titanium and titanium alloys, zirconia, etc. The implant 120 data may further include installation data and patient outcomes. The implant 120 data may include third-party data from the manufacturer of standardized or custom implant components 122. The implant 120 data may additionally include design for each connector 124 that join two or more implant components 122.

FIG. 5 depicts entries in an example substrate database, e.g., substrate database 142. The substrate database 142 stores substrate data that characterizes information about substrates 132 which may be used by the 3D printer 126 to print a structure such as an implant 120, implant component 122, or connector 124 for a patient. The substrate data may identify properties of the substrates 132, their methods of application and curing, and may additionally identify safety data and manufacturer information for the substrates 132. Some substrates 132 may be composed of two or more parts, such as a resin and hardener which cure after a working period which begins when the two components are mixed. Other substrates 132 may cure when exposed to a particular wavelength of light, such as ultraviolet. Further, some substrates 132 may require heat to allow the material to be extruded such as thermoplastics, while some substrates may be heated, melted, fused, bonded, etc. by a high intensity laser. The substrate database 142 may be populated by the manufacturers of the substrates 132 such as via the cloud 136 or a third-party database. The substrate database 142 is used by the customization module 146, simulation module 148, and the manufacturing module 150.

Figure 6:
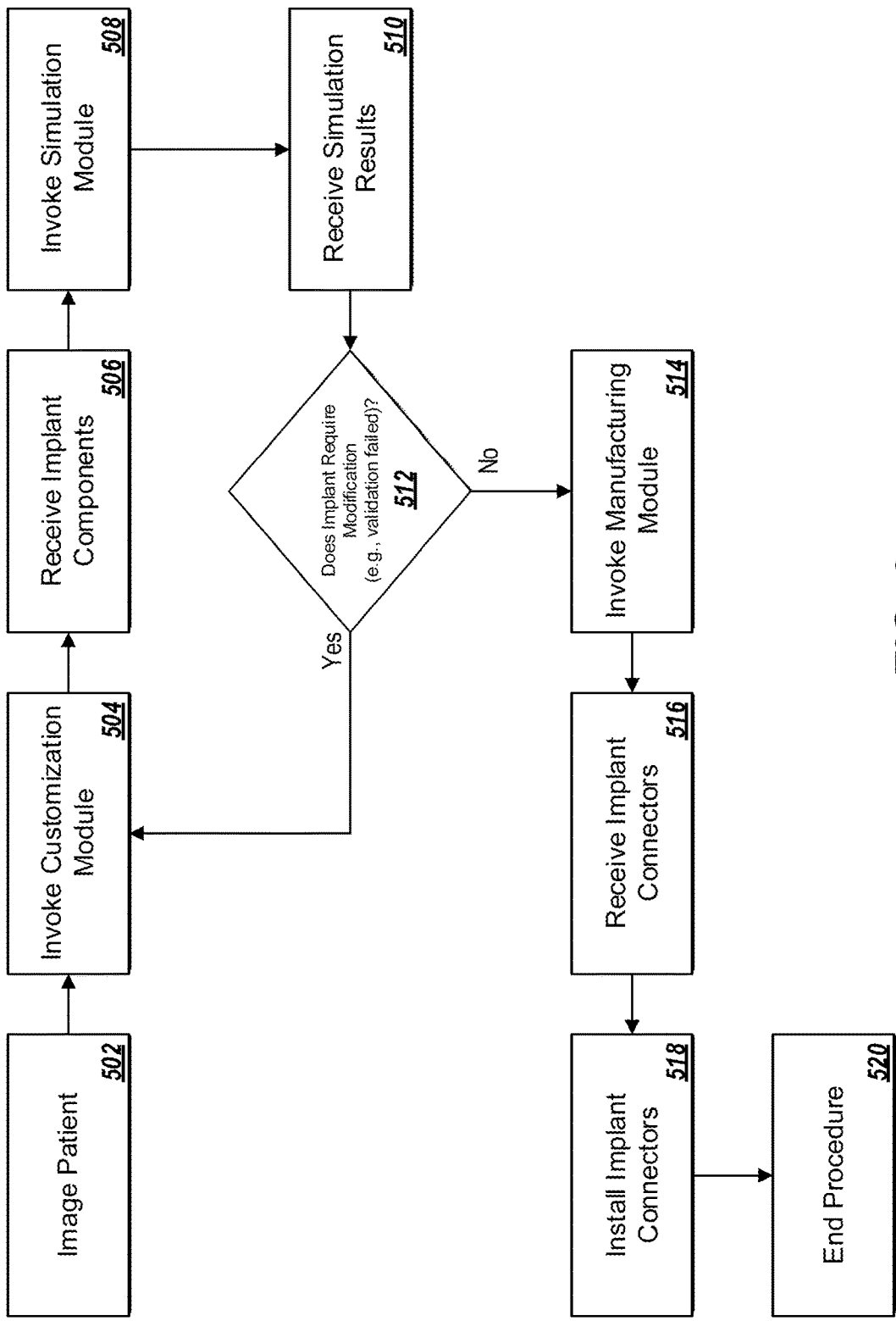
FIG. 6: Illustrates an example process performed by a base system for coordinating the design and installation of an implant with customized implant components and connectors for a patient.

Functioning of the base system, e.g., base system 144, will now be explained with reference to FIG. 6. More particularly, FIG. 6 depicts a flowchart of a process 600 coordinated by a base system 144 for manufacturing and installing an implant 120 in a patient. The process 600 can begin with imaging, at step 602, the patient, including imaging with an imaging device 118 the location (site) where an implant 120 is to be installed. The imaging may be performed using any suitable imaging techniques, including visual light modalities, radiologic modalities, or both. In some embodiments, at least one imaging modality is a radiologic modality such as CT, MRI, PET, etc. In some embodiments, a single imaging modality may be used, such as MRI. In other embodiments, multiple imaging modalities may be used such as MRI, CT and ultrasound. In some embodiments, a single image frame may be used. In other embodiments, multiple image frames may be used. When multiple image frames are used, multiple images may be used to create a higher resolution two-dimensional image. The same method can be applied in slices of varying depths, or from varying orientations to create a 3D representation of the print or implant site. As an example, imaging the right hip of a patient (e.g., John Smith) is done using MRI. The acquired image data may be further saved to the patient database 138.

Upon acquisition of the requisite image data, the base system 144 invokes, at step 604, the customization module 146. Customization module 146 receives the image data acquired from at least one imaging device 118. The customization module 146 queries the implant database 140 and selects an implant 120 design. From the implant 120 design, customization module 146 identifies a list of implant components 122 and selects standardized implant components 122 that will form the constituent parts of the implant 120. For each juncture between implant components 122 or implant components 122 and the patient's anatomy, customization module 140 designs at least one custom connector 124.

Customization module 140 continues to generate customized connector designs until a customized connector design has been developed for each connector 124 that is needed for a particular implant 120. Customization module 140 saves customized implant 120, implant components 122, and connectors 124 to the implant database 140.

The base system 144 receives, at step 606, data identifying customized implant components 122 and connectors 124 from the customization module 146. In some embodiments, at least one implant component 122 includes an integrated connector 124 customized to facilitate mating with another implant component 122 or the physiology of the patient. In some embodiments, at least one connector 124 is a discrete component physically separate from any implant component 122. The discrete connector 124 is intended to join either together with a discrete implant component 122, another connector 124, or to the physiology of the patient.

An example of a connector 124 may be a 3D printed hinge made of medical grade silicon comprising two sockets to accept ball shaped ends of two titanium alloy implant components 122. Another example is a titanium alloy implant component 122 which is shortened and into which connector 124 comprising a locking feature is created using a CNC mill such that the implant component 122 can be mated with another implant component 122 by sliding the two implant components 122 together along a first axis, while the joined implant components 122 will resist separation at the customized connector 124 in a second and third axis each perpendicular to the first axis.

At step 608, the base system 144 invokes simulation module 148. The simulation module 148 receives data that characterizes designs of the customized implant components 122 and connectors 124 from the base system 144, and simulates the interaction of implant components 122 and connectors 124 when assembled into an implant 120 and installed in a virtual representation of the patient based upon imaging data acquired by at least one imaging device 118.

Simulation module 148 determines from the simulations whether customized connectors 124 perform as expected (e.g., determines whether the customized connectors 124 perform within specified tolerances). The simulation module 148 may run simulations of an installation procedure for installing the implant 120 using implant components 122 and customized connectors 124, assembly of the implant components 122 and connectors 124 and may additionally comprise scenarios including weight loading, range of motion, endurance, etc. Implant components 122 or connectors 124 which do not meet predetermined performance parameters are added to an error log along with details of the simulations. The simulation results are further saved to the implant database 140.

At step 610, the base system 144 receives the simulation results from simulation module 148. The simulation results may include a binary pass versus fail result for the entire implant 120 assembly or a similar binary result for each implant component 122 and/or connector 124. The simulation results may further include detailed performance metrics, such as the type of simulations performed, physical tolerances, and predictions for range of motion, endurance, maximum load, etc. The simulation results may additionally comprise error log data related to implant components 122 or connectors 124 which may have failed to meet the predetermined performance parameters during simulation.

At step 612, the base system 144 determine whether one or more implant 120, implant components 122, or connectors 124 require modification. An implant 120, implant component 122, or connector 124 may require modification if it failed to meet the predetermined performance parameters during the one or more simulations. The performance parameters may be stored in the implant database 140, substrate database 142, or in a third-party database accessible via a cloud 136 such as a database belonging to the manufacturer of an implant component 122 or a standard setting organization for the performance of implants 120. The performance parameters may alternatively be determined by one or more medical professionals, such as a surgeon, or an engineer.

In some embodiments, the patient database 138 may additionally comprise data which may influence the performance parameters such as adjusting a metric to accommodate a patient's height, weight, age, normal level of physical activity, etc. For example, a connector 124 made of medical grade silicone may require modification if it is deformed more than 5 mm when subjected to a load of 100 kg. In another example, a connector 124 comprised of a modified titanium alloy implant component 122 may fail due to a measured tolerance of 2 mm between itself and the implant component 122 with which it was joined which exceeds a tolerance of 0.5 mm defined in the predetermined performance parameters.

At step 614, the base system 144 invokes manufacturing module 150. Base system 144 coordinates communication of final design data to the manufacturing module 150 for the implant components 122 and connectors 124 to be manufactured. The manufacturing module 150 can further query the substrate database 142 for the manufacturing processes and parameters for the substrate 132 from which each implant component 122 and connector 124 is to be printed. For each implant component 122 and/or connector 124 being manufactured or modified, the base system 144 or manufacturing module 150 selects an appropriate manufacturing tool, and directs the selected tools to perform the necessary manufacturing operations such as adding or removing material or otherwise modifying the shape or properties of the implant component 122 or connector 124. Manufacturing module 150 continues selecting appropriate tools and performing corresponding manufacturing operations according to the final design data until manufacture of the connector 124 is completed. Manufacturing module 150 repeats these operations to manufacture all implant components 122 or connectors requiring manufacture or modification.

At step 616, the base system 144 receives an indication that the manufacture of the implant components 122 and connectors 124 is completed. In response, the base system 144, at step 618, initiates installation of the implant 120. The implant 120 may be installed by a surgical robot 102, surgeon, or the combined effort of a surgical robot 102 and a surgeon. The implant 120 can be installed by inserting or otherwise attaching each implant component 122 and connector 124 to the patient and assembling the implant components 122 and connectors 124 into a final implant 120. The implant 120 may alternatively be partially or completely assembled prior to implantation in the patient. Installation and assembly of the implant components 122 or connectors 124 may require the expansion or other physical or chemical transformation of the implant components 122 or connectors 124.

In some embodiments, all or some of the implant components 122, connectors 124, or both, for an implant 120 may be manufactured in situ at the implant site. In some embodiments, all or some of the implant components 122, connectors 124, or both, for an implant 120 are manufactured ex situ, outside of the patient and the implant site. In some embodiments, a first subset of implant components 122 and/or connectors 124 are manufactured in situ, while a second subset of implant components 122 and/or connectors 124 are manufactured ex situ.

In some embodiments, the process 600 completes at step 620 when the implant 120 has been completely installed. Ending the procedure 500 can include removing surgical tools from the patient and closing any incisions. Ending the procedure 500 may further include taking any actions required during the procedure not previously mentioned to complete the surgical procedure and maintain the life and health of the patient. In some embodiments, removing all surgical tools from the patient and closing all incisions made to provide access to the implant site including to muscle, fascia, skin, etc. The patient can be further monitored for complications and to manage any conditions which may present.

Figure 7:
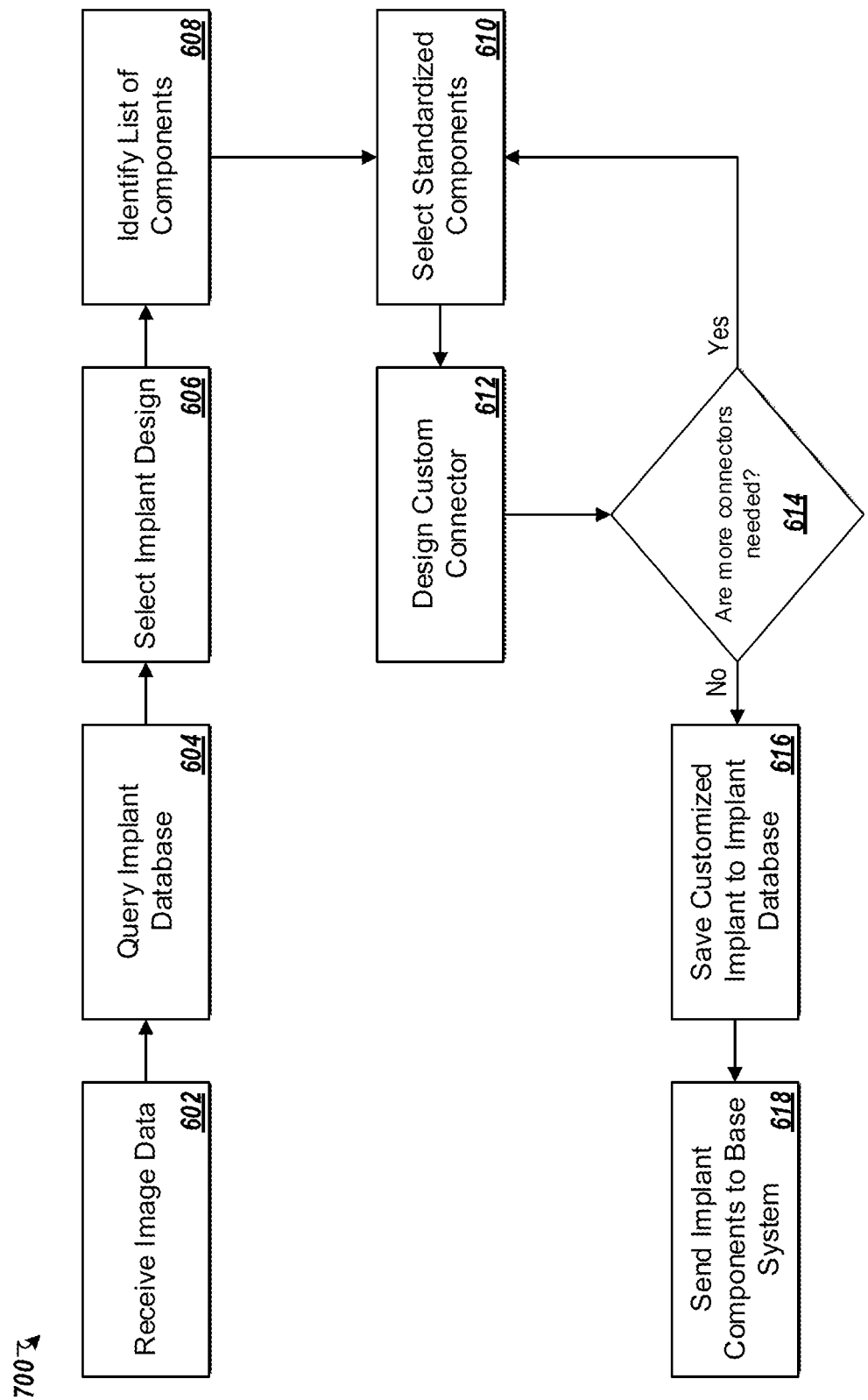
FIG. 7: Illustrates an example process performed by a customization module for customizing the design of implant components and connectors for a patient.

Functioning of the customization module, e.g., customization module 146, will now be explained with reference to FIG. 7. More particularly, FIG. 7 depicts a flowchart of a process 700 performed by the customization module 146 to generate a customized design for an implant 120. The process begins with receiving, at step 702, the image data from the base system 144. Alternatively, customization module 146 can receive a reference location or other identifying information to facilitate retrieval of the image data from the patient database 138. In some embodiments, the image data includes a series of MRI images compiled into a 3D model of the patient's physiology at the implant site, such as a 3D model of a portion of a pelvis where an implant 120 is to be installed (e.g., the right-side socket of the ball joint where the femur meets the pelvis).

At step 704, customization module 146 queries implant database 140 to obtain design data for the implant 120 that is to be installed. The implant 120 design may be specific to a particular anatomical structure for the type of implant 120 to be installed, such as a hip joint, or may be a generalized design for a category of implants 120, such as ball and socket joints. Similarly, the implant designs 120 may perform a specific structural task, such as reinforcing or fusing part of the spine. Customization module 146 can further query the substrate database 142 to identify biocompatible materials for the implant 120, and to identify their physical and chemical properties.

At step 706, customization module 146 selects an implant 120 design from the designs retrieved from the implant database 140. Alternatively, an implant 120 may be completely customized to meet the physiology or needs of the patient. Such implants 120 may be stored in the implant database 140 or may have been populated by a separate source, such as a third-party database or process accessible via the cloud 136 and which may or may not have been saved to the implant database 140. For example, customization module 146 may select a design for an artificial ball and socket joint which has been previously customized to fit the physiology of a particular patient (e.g., John Smith's right hip joint or an artificial hinge joint to replace Mr. Smith's left knee). As another example, the implant 120 may be a spinal implant such as for a fusion procedure comprising a series of implant components 122 including rods, plates, screws, and connectors 124.

At step 708, the customization module 146 identifies a list of implant components 122 and a list of implant connectors 124 necessary to manufacture the selected implant 120. The lists of implant components 122 and connectors 124 may be stored in the implant database 140, e.g., as a bill of materials, or may be dynamically generated by analyzing the implant design data. The list of implant components 122 may include standardized implant components 122, customized implant components 122, or both. Similarly, the listed connectors 124 may include standardized connectors 124, customized connectors 124, or both.

For a hip implant 120, the implant components 122 may include at least a socket to be affixed to the patient's pelvis which may be comprised of several segments which may be attached to each other and have multiple attachment points to the patient's pelvis. The hip implant 120 additionally can include a ball portion to be affixed to the patient's femur and designed to be captured by the socket attached to the pelvis. A knee implant 120 may comprise a hinge which may include at least a first plate, for mounting to the patient's femur, a second plate for mounting to the patient tibia, and a pin or other connector 124 for joining the first and second plates. A spinal implant 120 may comprise a plurality of rods, plates, screws, and other connectors 124.

At step 710, customization module 146 selects implant components 122 to be joined by a standard or custom connector 124. The implant components 122 may be standardized or custom or a combination of standardized and custom implant components 122. Alternatively, one or more implant components 122 may be selected to be mated to a tissue structure of the patient such as a bone. For example, customization module 146 may select the implant components 122 for a hip implant 120 comprising two segments of a socket to be affixed to the patient's pelvis. As another example, selecting the implant components 122 for a knee implant 120 can include selecting a first plate and a second plate. Selecting the implant components 122 for a spinal implant 120 can include selecting a rod and a screw.

At step 712, customization module 146 generates a design for a custom connector 124 to join the plurality of selected implant components 122 or the one or more implant components 122 to an anatomical structure of the patient. The customized connector 124 may be a discrete component or may be integrated with one or more implant components 122 by customizing the implant component 122 to incorporate a customized connector portion 124. To generate the custom design of a connector 124, customization module 146 can select one or more substrates 132 for the connector 124 from which the connector 124 will be manufactured. The connector 124 may be comprised of a single substrate 132 or may be a composite structure comprising multiple substrates 132. The design may further include manufacturing process instructions. The process instructions may comprise the type of operation to be completed such as additive manufacturing operations, including FDM, SLA, ALA, DLP, etc., subtractive manufacturing operations, or a collection or sequence of additive operations, subtractive operations, or both. The customized design may also specify parameters for one or more of the manufacturing operations, such as a working temperature and feed rate of the substrate 132, and the instructions, such as G-code, for directing a 3D printer 126, CNC mill 134, or other manufacturing equipment to manufacture or modify the implant component 122 or connector 124.

By way of example, generating the design for a customized connector 124 for the segments of a hip implant 120 socket can include selecting a standardized socket implant component 122, determining customization parameters for use in converting the standardized socket implant component 122 to a customized socket implant component 122, and generating manufacturing instructions that can be used to implement one or more manufacturing operations according to the customization parameters to physically realize (manufacture) the customized socket implant component 122. The customization parameters can include parameters defining dimensions, locations, and orientations for mating notches on the pair of implant socket segments such that the segments can slide relative to each other along one axis while resisting separation along any other axis. The instructions can specify one or more subtractive manufacturing techniques for milling or otherwise removing material from the standardized socket implant component 122 to form mating notches having the dimensions and other attributes defined by the customization parameters.

In another example, customization module 146 can generate a design for a customized connector 124 for a hip implant 120 to join a first plate and a second plate using a pin with a bend in the middle that creates a u-shaped depression at the midpoint of the pin. The pin can be made of a titanium alloy.

In another example, customization module 146 can generate a design for a customized connector 124 for a spinal implant 120 comprising a tulip-shaped connector that receives the rod through a first axis aligned to the side of the tulip shape, and that receives the screw through a second axis running through the opening of the tulip shape, wherein the second axis is substantially perpendicular to the first axis.

In some embodiments, customization module 146 can generate a design for a customized connector 124 to match the contour of a bone or other tissue of a patient, where the contour is derived from analysis of image data acquired from the at least one imaging device 118 (or analysis of a 3D model or representation of the bone or other tissue of the patient). For instance, the contour of an outer surface of one or more vertebrae of the spine can be determined as the shape of the surface in a 3D model of the vertebrae. Customization module 146 can then size and shape the mating side of connector 124 such that it complements the size and shape of a corresponding surface of the vertebrae. In this way, when manufactured, the connector 124 can be installed with its mating surface abutting the complementary surface of the vertebrae to achieve a secure fit in which substantially an entirety of the desired mating surface of the connector 124 aligns with the corresponding surface of the vertebrae within a specified tolerance, e.g., 0.1 mm, while providing a connection to at least one implant component 122 such as a rod or plate. Customization module 16 can use similar processes to customize the portion of connector 124 that mates with one or more implant components 122 so that the connector 124 can join the implant component(s) 122 to the vertebrae or other anatomical structure of the patient.

In another example, consider a patient that requires a knee replacement. The patient weighs 150 kg and is a professional weightlifter, although the standard implant hinge pin is only rated for 125 kg. A customized hinge pin connector is therefore required comprised of high strength materials and with a customized dimension such as adding an internal lattice structure to distribute the weight to achieve a modified hinge pin with a weight rating of 500 kg.

At step 714, customization module 146 determines whether additional connectors 124 are needed for the implant 120. No more connectors 124 are needed if each of the implant components 122 comprising the current implant 120 design can be sufficiently mated to one another and to the patient's physiology by the already completed connectors 124 as indicated by the image data acquired from at least one imaging device 118. If an implant component 122 remains without a means of being attached to the rest of the implant 120, then more connectors 124 are needed. If more connectors 124 are needed, then the process 700 returns to step 710, and customization module 146 selects additional implant components 122 to be joined.

At step 716, customization module 146 saves files for the customized implant 120, implant components 122, and connectors 124 to the implant database 140 when all of the implant components 122 or connectors have been customized as necessary. At step 718, customization module 146 sends the implant components 122, connectors 124, and all related information necessary to manufacture the customized implant components 122 and connectors to the base system 144. The implant components 122 may comprise both standardized and customized, or modified and unmodified implant components 122. The connectors 124 may be discrete components for joining one or more implant components 122 together or to tissue structures of the patient, may be modified parts of implant components 122, or a combination of both.

Figure 8:
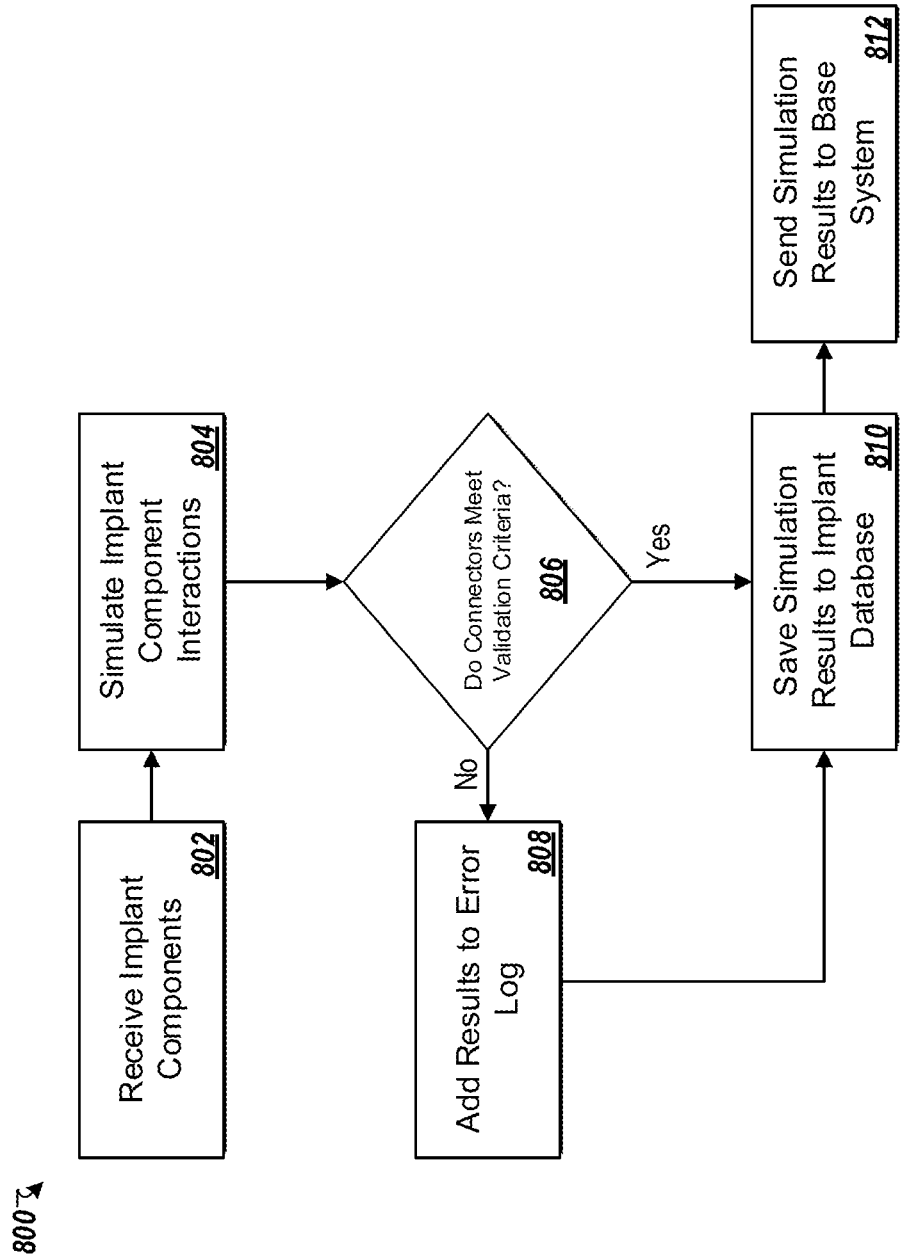
FIG. 8: Illustrates an example process performed by a simulation module for assessing the performance of customized implant components and connectors.

Functioning of the simulation module, e.g., simulation module 148, will now be explained with reference to FIG. 8. More particularly, FIG. 8 depicts a flowchart of a process 800 performed by the customization module 148 to generate a customized design for an implant 120.

Process 800 begins with the simulation module 148 receiving, at step 802, implant data describing the implant components 122 and connectors 124 for an at least partially customized implant 120 from the base system 144. The implant components 122 and connectors 124 are capable of being assembled to form an implant 120. Simulation module 148 further receives data characterizing the design, installation, and manufacture information about the implant components 122 and connectors 124 including any information necessary to manufacture the connectors 124 from substrate 132 or by modifying standardized or custom implant components 122. The information required for assembly may comprise procedure data from a patient database or a third-party database accessible via a cloud 136. The third-party database may be from a manufacturer of implants 120 or implant components 122 or compiled data from one or more medical facilities.

At step 804, simulation module 148 generates, executes, and analyzes simulations of the interactions between implant components 122, connectors 124, and patient anatomical structures (e.g., bones or other tissue at the implant site). In some implementations, simulations are performed on a standalone assembly of implant components 122, connectors 124, or both, apart from the patient's physiology (i.e., apart from anatomical structures of the patient).

Simulations may use image data from at least one imaging device 118 of the patient to simulate the installation and assembly of the implant components 122 and connectors 124 to form the implant 120 in a virtual representation of the patient. The simulation may alternatively be performed in a standard anatomical model which may be altered based upon the acquired image data of the patient. The simulations may test for multiple scenarios including loading, flexion, rotational forces, etc. The simulations may be performed on all implant components 122 and connectors 124 simultaneously or may be performed on each implant component 122 and connector 124 independently. The simulations monitoring the physical dimensions of the implant components 122 and connectors 124 and the virtual representation of the patient's anatomy including deformations, displacements, and other metrics which may indicate a failure of an implant component 122 or connector 124.

In some embodiments, simulation module 148 is configured to simulate the manufacture of the implant components 122 and connectors 12. In such examples, the simulations may determine whether the implant components 122 or connectors 124 can be manufactured using available methods using the specified substrates 132.

At step 806, simulation module 148 determines whether the implant components 122 and connectors 124 perform as expected by comparing the metrics monitored during the simulations to a set of predetermined thresholds which may be stored in the implant database 140, patient database 138, substrate database 142, a third-party database or source accessible via a cloud 136, or which may be manually specified by a surgeon, engineer, or other technician. An example of a threshold may be a tolerance of no more than 0.5 mm of space between mated implant components 122, connectors 124, or the patient's physiology. If a simulation predicts a gap of 2 mm between an implant component 122 and a connector 124, and if the gap exceeds the maximum allowed tolerance (e.g., 0.5 mm), then the connector 124 does not perform as expected, which may indicate that the implant component 122, connector 124, or both, require further modification by customization module 146 to improve performance. In an alternate embodiment, a connector 124 may be allowed to deform up to 3 mm when subjected to a 100 kg load, therefore a deformation of 5 mm would be considered a failure.

Similarly, simulation module 146 can perform simulations of the modification or manufacture of an implant component 122 or connector 124 such as simulation of 3D printing. These simulations may indicate where a manufacturing operation may be subject to failure and where modification of the manufacturing process may be required, such as the addition of removable support material for a 3D print on a 3D printer 126. Similar programs can be used for subtractive manufacturing methods such as when using a CNC mill 134.

At step 808, simulation module 148 adds simulation results to an error log if the implant components 122 or connectors 124 do not perform as expected/failed to meet one or more performance criteria. The error log may comprise issues, relevant data, and may also include data indicating modification(s) to be made either to the design of an implant component 122, connector 124, or the implantation and assembly procedure or the manufacture or modification of the implant components 122 and connectors 124.

At step 810, simulation module 148 stores the simulation results to the implant database 140. The simulation results may comprise the error data compiled in step 808. The simulation results may also comprise the performance metrics and other metrics and simulation results obtained from the simulations. The simulation results data may include values for measurements taken continuously for a period of time in a simulation, and/or may include statistics calculated from the simulation results such as an average (e.g., mean or median), maximum, and minimum values for particular metrics.

At step 812, simulation module 148 sends the simulation results to base system 144. The simulation results may comprise a binary pass versus fail result for the entire implant 120 assembly or a similar binary result for each implant component 122 and/or connector 124. The simulation results may further comprise detailed performance metrics, such as the type of simulations performed, physical tolerances, and predictions for range of motion, endurance, maximum load, etc. The simulation results may additionally comprise the error log data.

Figure 9:
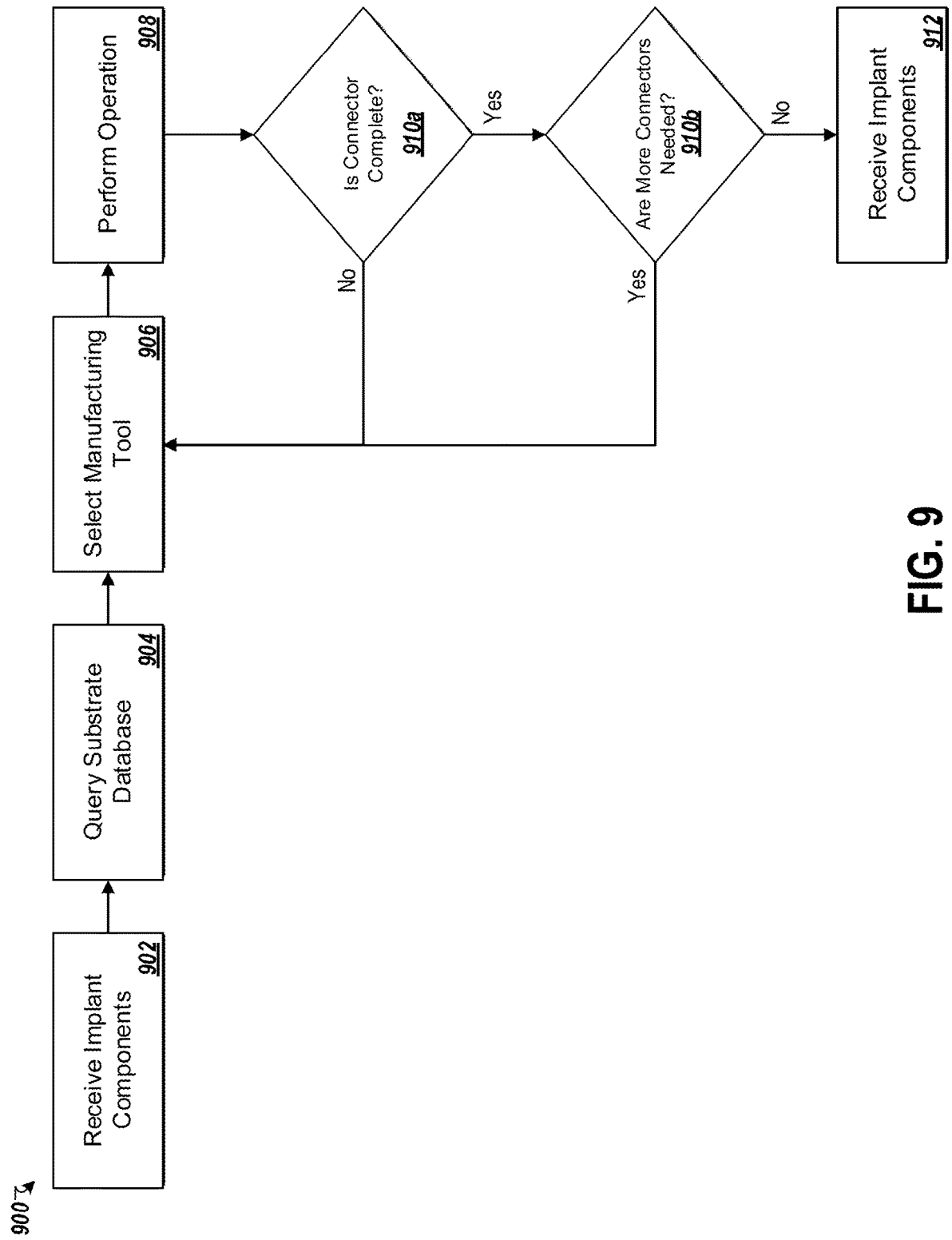
FIG. 9: Illustrates an example process performed by a manufacturing module for manufacturing customized implant components and connectors.

Functioning of the manufacturing module, e.g., manufacturing module 150, will now be explained with reference to FIG. 9. More particularly, FIG. 9 depicts a flowchart of a process 900 performed by the manufacturing module 150 to manufacture a customized implant 120.

At step 902, manufacturing module 150 receives designs for customized implant components 122 and connectors 124 from the base system 144. In some embodiments, at least one implant component 122 has a portion of its mass comprising a connector 124 customized to facilitate mating with another implant component 122 or the physiology of the patient. In some embodiments, at least one connector 124 is a discrete component separate from the implant components 122 it is intended to join either together or to the physiology of the patient. The implant component 122 and connector 124 data additionally identify the substrates 132 to be used and instructions for one or more manufacturing processes for the manufacture or modification of each implant component 122 and connector 124.

At step 904, manufacturing module 150 queries the substrate database 142 for substrate 132 properties. The substrate 132 properties may include working temperatures, feed rates, and appropriate manufacturing methods, such as a type of 3D printer 126 to use, or the tooling for subtractive manufacturing methods such as a CNC mill 134 for each implant component 122 or connector 124 to be modified or manufactured.

At step 906, manufacturing module 150 selects one or more manufacturing tools to use in completing a manufacturing process to manufacture the implant 150. A manufacturing tool may be an additive manufacturing machine such as a 3D printer 126, a subtractive manufacturing machine such as a CNC mill 134 or router, or may alternatively be an apparatus for modifying an implant component 122 which adds bends or other modifications to an implant component 122 or connector 124. A manufacturing tool may additionally refer to an apparatus for thermally, chemically, or otherwise treating a substrate 132 to change the properties of the substrate 132. In an embodiment, manufacturing module 150 selects an SLS 3D printer 126 to manufacture a connector 124 from a titanium substrate 132. In another embodiment, manufacturing module selects a CNC mill 134 to remove 5 mm from an implant component 122 and to shape a connector 124 comprising a notch in one end of the implant component 122.

At step 908, manufacturing module 150 directs performance of a manufacturing operation using the selected manufacturing tool. For example, manufacturing module 150 may provide instructions to an SLS 3D printer 126 to initiate printing of a connector 124 from a titanium material. In another example, manufacturing module 150 may direct an SLA 3D printer 126 to print a resin connector 124. In a further embodiment, manufacturing module 150 may coordinate with a controller of a CNC mill 124 to cause the CNC mill 124 to carve the end of a rod-shaped implant component 122 to form a ball shape. The rod being further bent to an angle of 30°.

At step 910, manufacturing module 150 determines whether the manufacture of connector 124 is complete. In general, a connector 124 is complete if the manufactured part matches the specification dictated by the design of the connector 124. Alternatively, the connector 124 is complete if there are no further manufacturing instructions as all provided instructions have been completed. In some embodiments, the connector 124 is deemed complete after a visual inspection or an inspection by an automated system using an imaging device 118 to image the connector 124. A robotic arm 112 may additionally grip the connector 124 using an end effector 114 and manipulate the connector 124 as part of the inspection. If the connector 124 is not complete, manufacturing module 150 may return to step 906 and select a manufacturing tool to continue manufacturing the connector 124.

At step 912, manufacturing module 150 determines whether more connectors 124 need to be manufactured or implant components 122 modified. If all connectors 124 have been created based upon the designs received from the base system 144, then no further connectors are needed. If more connectors are needed, process 900 returns to step 906, and the manufacturing module 150 selects a manufacturing tool and implant component 122 or connector 124 to modify or manufacture. At step 914, manufacturing module 150 provides the modified and manufactured implant components 122 and connectors 124 to the base system 144.

In this specification, a computer subsystem, module, or engine can be implemented on one or more computers in one or more locations, and can encompass both the software and hardware aspects of the computer(s) that carry out the respective functions of the subsystem, module, or engine.

Figure 10:
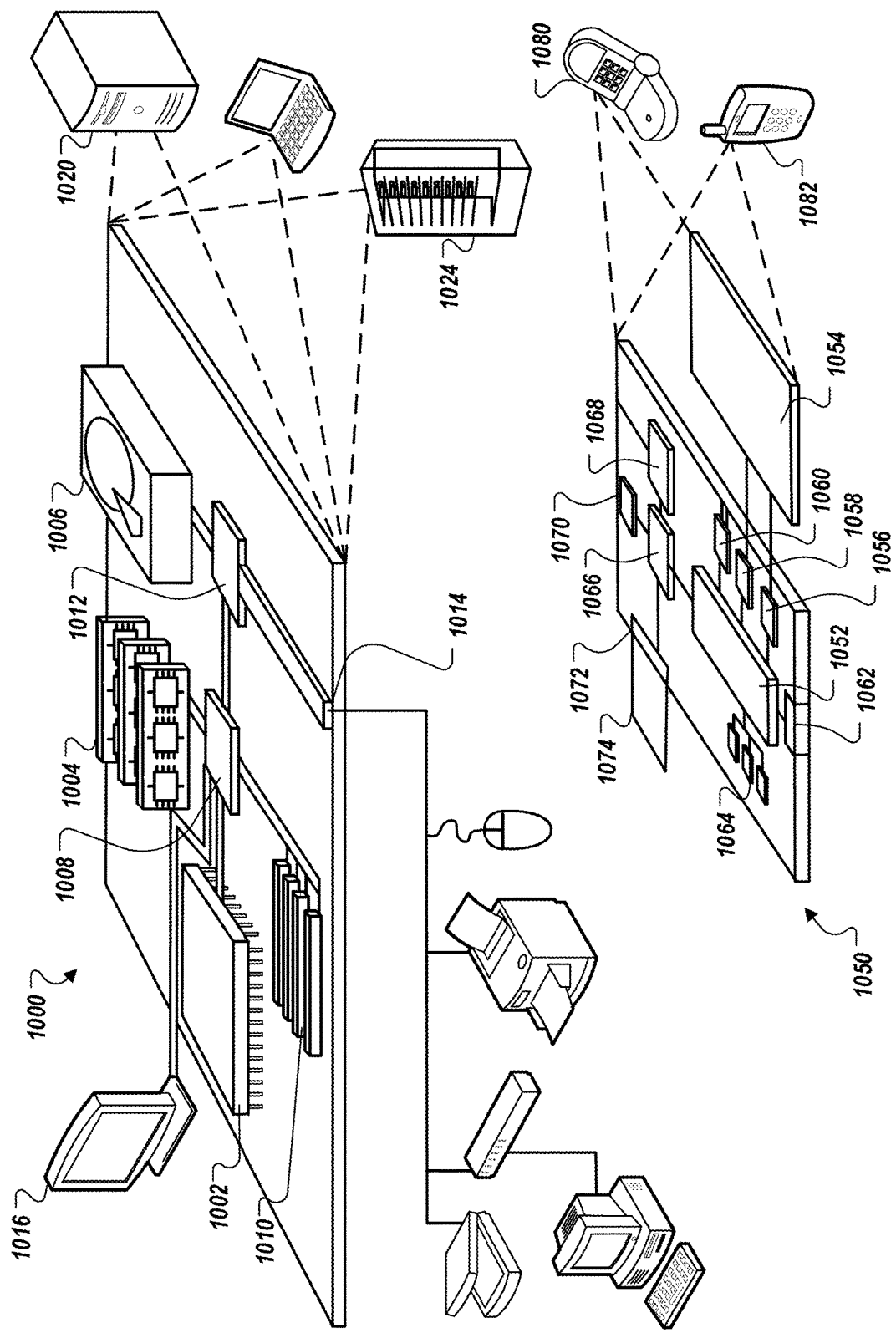
FIG. 10: Illustrates components of example computing devices that can be used to carry out computer-implemented aspects of the present disclosure.

FIG. 10 shows an example of a computing device 1000 and an example of a mobile computing device that can be used to implement the techniques described here. The computing device 1000 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1000 includes a processor 1002, a memory 1004, a storage device 1006, a high-speed interface 1008 connecting to the memory 1004 and multiple high-speed expansion ports 1010, and a low-speed interface 1012 connecting to a low-speed expansion port 1014 and the storage device 1006. Each of the processor 1002, the memory 1004, the storage device 1006, the high-speed interface 1008, the high-speed expansion ports 1010, and the low-speed interface 1012, are interconnected using various busses, and can be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as a display 1016 coupled to the high-speed interface 1008. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1004 stores information within the computing device 1000. In some implementations, the memory 1004 is a volatile memory unit or units. In some implementations, the memory 1004 is a non-volatile memory unit or units. The memory 1004 can also be another form of computer-readable medium, such as a magnetic or optical disk.

The storage device 1006 is capable of providing mass storage for the computing device 1000. In some implementations, the storage device 1006 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1004, the storage device 1006, or memory on the processor 1002.

The high-speed interface 1008 manages bandwidth-intensive operations for the computing device 1000, while the low-speed interface 1012 manages lower bandwidth-intensive operations. Such allocation of functions is exemplary only. In some implementations, the high-speed interface 1008 is coupled to the memory 1004, the display 1016 (e.g., through a graphics processor or accelerator), and to the high-speed expansion ports 1010, which can accept various expansion cards (not shown). In the implementation, the low-speed interface 1012 is coupled to the storage device 1006 and the low-speed expansion port 1014. The low-speed expansion port 1014, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1000 can be implemented in a number of different forms, as shown in the figure. For example, it can be implemented as a standard server 1020, or multiple times in a group of such servers. In addition, it can be implemented in a personal computer such as a laptop computer 1022. It can also be implemented as part of a rack server system 1024. Alternatively, components from the computing device 1000 can be combined with other components in a mobile device (not shown), such as a mobile computing device 1050. Each of such devices can contain one or more of the computing device 1000 and the mobile computing device 1050, and an entire system can be made up of multiple computing devices communicating with each other.

The mobile computing device 1050 includes a processor 1052, a memory 1064, an input/output device such as a display 1054, a communication interface 1066, and a transceiver 1068, among other components. The mobile computing device 1050 can also be provided with a storage device, such as a micro-drive or other device, to provide additional storage. Each of the processor 1052, the memory 1064, the display 1054, the communication interface 1066, and the transceiver 1068, are interconnected using various buses, and several of the components can be mounted on a common motherboard or in other manners as appropriate.

The processor 1052 can execute instructions within the mobile computing device 1050, including instructions stored in the memory 1064. The processor 1052 can be implemented as a chipset of chips that include separate and multiple analog and digital processors. The processor 1052 can provide, for example, for coordination of the other components of the mobile computing device 1050, such as control of user interfaces, applications run by the mobile computing device 1050, and wireless communication by the mobile computing device 1050.

The processor 1052 can communicate with a user through a control interface 1058 and a display interface 1056 coupled to the display 1054. The display 1054 can be, for example, a TFT (Thin-Film-Transistor Liquid Crystal Display) display or an OLED (Organic Light Emitting Diode) display, or other appropriate display technology. The display interface 1056 can comprise appropriate circuitry for driving the display 1054 to present graphical and other information to a user. The control interface 1058 can receive commands from a user and convert them for submission to the processor 1052. In addition, an external interface 1062 can provide communication with the processor 1052, so as to enable near area communication of the mobile computing device 1050 with other devices. The external interface 1062 can provide, for example, for wired communication in some implementations, or for wireless communication in other implementations, and multiple interfaces can also be used.

The memory 1064 stores information within the mobile computing device 1050. The memory 1064 can be implemented as one or more of a computer-readable medium or media, a volatile memory unit or units, or a non-volatile memory unit or units. An expansion memory 1074 can also be provided and connected to the mobile computing device 1050 through an expansion interface 1072, which can include, for example, a SIMM (Single In Line Memory Module) card interface. The expansion memory 1074 can provide extra storage space for the mobile computing device 1050, or can also store applications or other information for the mobile computing device 1050. Specifically, the expansion memory 1074 can include instructions to carry out or supplement the processes described above, and can include secure information also. Thus, for example, the expansion memory 1074 can be provide as a security module for the mobile computing device 1050, and can be programmed with instructions that permit secure use of the mobile computing device 1050. In addition, secure applications can be provided via the SIMM cards, along with additional information, such as placing identifying information on the SIM M card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1064, the expansion memory 1074, or memory on the processor 1052. In some implementations, the computer program product can be received in a propagated signal, for example, over the transceiver 1068 or the external interface 1062.

The mobile computing device 1050 can communicate wirelessly through the communication interface 1066, which can include digital signal processing circuitry where necessary. The communication interface 1066 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1068 using a radio-frequency. In addition, short-range communication can occur, such as using a Bluetooth, WiFi, or other such transceiver (not shown). In addition, a GPS (Global Positioning System) receiver module 1070 can provide additional navigation- and location-related wireless data to the mobile computing device 1050, which can be used as appropriate by applications running on the mobile computing device 1050.

The mobile computing device 1050 can also communicate audibly using an audio codec 1060, which can receive spoken information from a user and convert it to usable digital information. The audio codec 1060 can likewise generate audible sound for a user, such as through a speaker, e.g., in a handset of the mobile computing device 1050. Such sound can include sound from voice telephone calls, can include recorded sound (e.g., voice messages, music files, etc.) and can also include sound generated by applications operating on the mobile computing device 1050.

The mobile computing device 1050 can be implemented in a number of different forms, as shown in the figure. For example, it can be implemented as a cellular telephone 1080. It can also be implemented as part of a smart-phone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as disclosed above.

The invention claimed is:

1. A method for customizing connectors for prosthetic implants, comprising:

identifying a prosthetic implant for a particular patient, the prosthetic implant comprising a plurality of implant components that form the prosthetic implant when assembled;

identifying that the prosthetic implant requires a customized implant connector to secure at least one of the plurality of implant components to an anatomical structure of the particular patient;

obtaining at least one image of the particular patient, the at least one image depicting an implantation site that includes the anatomical structure of the particular patient;

analyzing the at least one image of the particular patient to determine a profile of the implantation site, the profile including data that characterizes a geometry of a mating surface region of the anatomical structure of the particular patient, the mating surface region identified as an area where the customized implant connector is planned to mate with the anatomical structure;

identifying a standardized implant connector, wherein a design of the standardized implant connector was developed substantially independently of the particular patient;

customizing the design of the standardized implant connector to generate a design for the customized implant connector that is personalized to the patient, including (i) sizing and shaping an adhesion site for the customized implant connector to have a geometry that complements the geometry of the mating surface region of the anatomical structure of the particular patient within a first tolerance level and (ii) sizing and shaping a non-adhesion portion of the customized implant connector to have a geometry that corresponds to a geometry of a non-mating surface region of the anatomical structure of the particular patient within a second tolerance level, wherein the second tolerance level is less restrictive than the first tolerance level and is determined based on a distance between the non-adhesion portion of the customized implant connector and the adhesion site;

selecting a manufacturing tool for manufacturing a physical instance of the customized implant connector, based on one or more physical properties of a substrate of the customized implant connector;

providing manufacturing instructions that direct performance of a manufacturing operation using the selected manufacturing tool, to manufacture the physical instance of the customized implant connector; and after the manufacturing instructions have been completed using the selected manufacturing tool, performing an automated visual inspection of the physical instance of the customized implant connector, wherein the customized implant connector is manipulated by an end effector of a robotic arm in view of an imaging device during the automated visual inspection.

2. The method of claim 1, wherein the prosthetic implant comprises a hip implant, a knee implant, or a spinal implant.

3. The method of claim 1, comprising implanting the prosthetic implant in the particular patient, including using the physical instance of the customized implant connector to secure the at least one of the plurality of implant components to the anatomical structure of the particular patient.

4. The method of claim 1, comprising manufacturing the physical instance of the customized implant connector in situ at the implantation site of the particular patient.

5. The method of claim 1, wherein:

the manufacturing tool comprises a three-dimensional (3D) printer and the manufacturing operation comprises an additive manufacturing process performed by the 3D printer; or the manufacturing tool comprises a computer numerical control (CNC) machining tool and the manufacturing operation comprises a subtractive manufacturing process performed by the CNC machining tool.

6. The method of claim 1, comprising validating the design of the customized implant connector before providing the manufacturing instructions that direct performance of the manufacturing operation using the selected manufacturing tool.

7. The method of claim 6, wherein validating the design of the customized implant connector comprises:

simulating use of the customized implant connector to secure at least one of the plurality of implant components to the anatomical structure of the particular patient; and obtaining simulation results that include simulated performance metrics for the customized implant connector; and comparing the simulated performance metrics for the customized implant connector to one or more validation criteria to inform a determination whether to reject or accept the design of the customized implant connector.

8. The method of claim 7, wherein the simulated performance metrics for the customized implant connector comprise at least one of a load metric or a range of motion metric, wherein comparing the simulated performance metrics for the customized implant connector to the one or more validation criteria comprises determining whether a first simulated performance metric falls within an acceptable range for the first simulated performance metric.

9. The method of claim 7, comprising, in response to a determination that the design of the customized implant connector failed to satisfy at least one of the validation criteria, adjusting the design of the customized implant connector and repeating the simulating, obtaining of simulation results, and comparing of the simulated performance metrics to the one or more validation criteria with respect to the adjusted design of the customized implant connector.

10. The method of claim 1, wherein the customized implant connector is integrally formed in one of the plurality of implant components.

11. The method of claim 1, wherein the customized implant connector is a discrete item separate from any of the plurality of implant components.

12. The method of claim 1, wherein analyzing the at least one image of the particular patient to determine a profile of the implantation site comprises generating a three-dimensional (3D) model of the implantation site including the anatomical structure of the particular patient, wherein the geometry of the mating surface region of the anatomical structure of the particular patient is derived from the 3D model.

13. The method of claim 1, wherein customizing the design of the standardized implant connector to generate the design for the customized implant connector comprises selecting a bio-compatible substrate material from which to manufacture the physical instance of the standardized implant connector.

14. The method of claim 1, wherein customizing the design of the standardized implant connector to generate the design for the customized implant connector comprises shaping the customized implant connector to provide an interface for mating with one or more implant components.

15. A system for customizing connectors for prosthetic implants, comprising:

one or more processors; and one or more non-transitory computer-readable media having instructions stored thereon that, when executed by the one or more processors, cause performance of operations comprising:

identifying a prosthetic implant for a particular patient, the prosthetic implant comprising a plurality of implant components that form the prosthetic implant when assembled;

identifying that the prosthetic implant requires a customized implant connector to secure at least one of the plurality of implant components to an anatomical structure of the particular patient;

obtaining at least one image of the particular patient, the at least one image depicting an implantation site that includes the anatomical structure of the particular patient;

analyzing the at least one image of the particular patient to determine a profile of the implantation site, the profile including data that characterizes a geometry of a mating surface region of the anatomical structure of the particular patient, the mating surface region identified as an area where the customized implant connector is planned to mate with the anatomical structure;

identifying a standardized implant connector, wherein a design of the standardized implant connector was developed substantially independently of the particular patient;

customizing the design of the standardized implant connector to generate a design for the customized implant connector that is personalized to the patient, including (i) sizing and shaping an adhesion site for the customized implant connector to have a geometry that complements the geometry of the mating surface region of the anatomical structure of the particular patient within a first tolerance level and (ii) sizing and shaping a non-adhesion portion of the customized implant connector to have a geometry that corresponds to a geometry of a non-mating surface region of the anatomical structure of the particular patient within a second tolerance level, wherein the second tolerance level is less restrictive than the first tolerance level and is determined based on a distance between the non-adhesion portion of the customized implant connector and the adhesion site;

selecting a manufacturing tool for manufacturing a physical instance of the customized implant connector, based on one or more physical properties of a substrate of the customized implant connector;

providing manufacturing instructions that direct performance of a manufacturing operation using the selected manufacturing tool, to manufacture the physical instance of the customized implant connector; and after the manufacturing instructions have been completed using the selected manufacturing tool, performing an automated visual inspection of the physical instance of the customized implant connector, wherein the customized implant connector is manipulated by an end effector of a robotic arm in view of an imaging device during the automated visual inspection.

16. The system of claim 15, wherein the prosthetic implant comprises a hip implant, a knee implant, or a spinal implant.

17. The system of claim 15, wherein the operations comprise implanting the prosthetic implant in the particular patient, including using the physical instance of the customized implant connector to secure the at least one of the plurality of implant components to the anatomical structure of the particular patient.

18. The system of claim 15, wherein the operations comprise manufacturing the physical instance of the customized implant connector in situ at the implantation site of the particular patient.

19. The system of claim 15, wherein:

the manufacturing tool comprises a three-dimensional (3D) printer and the manufacturing operation comprises an additive manufacturing process performed by the 3D printer; or the manufacturing tool comprises a computer numerical control (CNC) machining tool and the manufacturing operation comprises a subtractive manufacturing process performed by the CNC machining tool.

20. The system of claim 15, wherein the operations comprise validating the design of the customized implant connector before providing the manufacturing instructions that direct performance of the manufacturing operation using the selected manufacturing tool.

21. The system of claim 20, wherein validating the design of the customized implant connector comprises:
   simulating use of the customized implant connector to secure at least one of the plurality of implant components to the anatomical structure of the particular patient; and
   obtaining simulation results that include simulated performance metrics for the customized implant connector; and
   comparing the simulated performance metrics for the customized implant connector to one or more validation criteria to inform a determination whether to reject or accept the design of the customized implant connector.

22. The system of claim 21, wherein the simulated performance metrics for the customized implant connector comprise at least one of a load metric or a range of motion metric, wherein comparing the simulated performance metrics for the customized implant connector to the one or more validation criteria comprises determining whether a first simulated performance metric falls within an acceptable range for the first simulated performance metric.

23. The system of claim 21, wherein the operations comprise, in response to a determination that the design of the customized implant connector failed to satisfy at least one of the validation criteria, adjusting the design of the customized implant connector and repeating the simulating, obtaining of simulation results, and comparing of the simulated performance metrics to the one or more validation criteria with respect to the adjusted design of the customized implant connector.

24. The system of claim 15, wherein the customized implant connector is integrally formed in one of the plurality of implant components.

25. The system of claim 15, wherein the customized implant connector is a discrete item separate from any of the plurality of implant components.

26. The system of claim 15, wherein analyzing the at least one image of the particular patient to determine a profile of the implantation site comprises generating a three-dimensional (3D) model of the implantation site including the anatomical structure of the particular patient, wherein the geometry of the mating surface region of the anatomical structure of the particular patient is derived from the 3D model.

27. The system of claim 15, wherein customizing the design of the standardized implant connector to generate the design for the customized implant connector comprises selecting a bio-compatible substrate material from which to manufacture the physical instance of the standardized implant connector.

28. One or more non-transitory computer-readable media having instructions stored thereon that, when executed by one or more computers, cause performance of operations comprising:
   identifying a prosthetic implant for a particular patient, the prosthetic implant comprising a plurality of implant components that form the prosthetic implant when assembled;
   identifying that the prosthetic implant requires a customized implant connector to secure at least one of the plurality of implant components to an anatomical structure of the particular patient;
   obtaining at least one image of the particular patient, the at least one image depicting an implantation site that includes the anatomical structure of the particular patient;
   analyzing the at least one image of the particular patient to determine a profile of the implantation site, the profile including data that characterizes a geometry of a mating surface region of the anatomical structure of the particular patient, the mating surface region identified as an area where the customized implant connector is planned to mate with the anatomical structure;
   identifying a standardized implant connector, wherein a design of the standardized implant connector was developed substantially independently of the particular patient;
   customizing the design of the standardized implant connector to generate a design for the customized implant connector that is personalized to the patient, including (i) sizing and shaping an adhesion site for the customized implant connector to have a geometry that complements the geometry of the mating surface region of the anatomical structure of the particular patient within a first tolerance level and (ii) sizing and shaping a non-adhesion portion of the customized implant connector to have a geometry that corresponds to a geometry of a non-mating surface region of the anatomical structure of the particular patient within a second tolerance level, wherein the second tolerance level is less restrictive than the first tolerance level and is determined based on a distance between the non-adhesion portion of the customized implant connector and the adhesion site;
   selecting a manufacturing tool for manufacturing a physical instance of the customized implant connector, based on one or more physical properties of a substrate of the customized implant connector;
   providing manufacturing instructions that direct performance of a manufacturing operation using the selected manufacturing tool, to manufacture the physical instance of the customized implant connector; and
   after the manufacturing instructions have been completed using the selected manufacturing tool, performing an automated visual inspection of the physical instance of the customized implant connector, wherein the customized implant connector is manipulated by an end effector of a robotic arm in view of an imaging device during the automated visual inspection.

29. The method of claim 1, wherein the non-adhesion portion of the customized implant connector is a first non-adhesion portion that is located a first distance from the adhesion site, the method comprising applying a third tolerance level for customizing a second non-adhesion portion of the customized implant connector, the third tolerance level being less restrictive than the second tolerance level based on the second non-adhesion portion being located a second distance from the adhesion site that is greater than the first distance.

* * * * *